United States Patent
Hung et al.

(10) Patent No.: US 11,136,577 B2
(45) Date of Patent: Oct. 5, 2021

(54) METHODS AND COMPOSITIONS FOR INHIBITING PMP22 EXPRESSION

(71) Applicant: Ionis Pharmaceuticals, Inc., Carlsbad, CA (US)

(72) Inventors: Gene Hung, San Diego, CA (US); Holly Kordasiewicz, San Diego, CA (US); Hien Thuy Zhao, San Diego, CA (US); Eric E. Swayze, Encinitas, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 16/083,086

(22) PCT Filed: Mar. 9, 2017

(86) PCT No.: PCT/US2017/021534
§ 371 (c)(1),
(2) Date: Sep. 7, 2018

(87) PCT Pub. No.: WO2017/156242
PCT Pub. Date: Sep. 14, 2017

(65) Prior Publication Data
US 2019/0062741 A1    Feb. 28, 2019

Related U.S. Application Data

(60) Provisional application No. 62/305,959, filed on Mar. 9, 2016.

(51) Int. Cl.
| | | |
|---|---|---|
| *C12N 15/113* | (2010.01) |
| *A61P 25/02* | (2006.01) |
| *A61K 9/00* | (2006.01) |
| *A61P 25/28* | (2006.01) |
| *A61K 31/7088* | (2006.01) |

(52) U.S. Cl.
CPC ......... *C12N 15/113* (2013.01); *A61K 9/0019* (2013.01); *A61K 31/7088* (2013.01); *A61P 25/02* (2018.01); *A61P 25/28* (2018.01); *C12N 2310/11* (2013.01); *C12N 2310/315* (2013.01); *C12N 2310/321* (2013.01); *C12N 2310/322* (2013.01); *C12N 2310/3231* (2013.01); *C12N 2310/3341* (2013.01); *C12N 2310/341* (2013.01); *C12N 2310/346* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,845,205 A | 7/1989 | Huynh Dinh et al. |
| 5,034,506 A | 7/1991 | Summerton et al. |
| 5,130,302 A | 7/1992 | Spielvogel et al. |
| 5,134,066 A | 7/1992 | Rogers et al. |
| 5,166,315 A | 11/1992 | Summerton et al. |
| 5,175,273 A | 12/1992 | Bischofberger et al. |
| 5,185,444 A | 12/1993 | Summerton et al. |
| 5,367,066 A | 11/1994 | Urdea et al. |
| 5,432,272 A | 7/1995 | Benner |
| 5,434,257 A | 7/1995 | Matteucci |
| 5,457,187 A | 10/1995 | Gmelner et al. |
| 5,457,191 A | 10/1995 | Cook et al. |
| 5,459,255 A | 10/1995 | Cook et al. |
| 5,484,908 A | 1/1996 | Froehler et al. |
| 5,502,177 A | 3/1996 | Matteucci et al. |
| 5,525,711 A | 6/1996 | Hawkins et al. |
| 5,552,540 A | 9/1996 | Haralambidis |
| 5,587,469 A | 12/1996 | Cook et al. |
| 5,587,470 A | 12/1996 | Cook et al. |
| 5,594,121 A | 1/1997 | Froehler et al. |
| 5,596,091 A | 1/1997 | Switzer |
| 5,614,617 A | 3/1997 | Cook et al. |
| 5,645,985 A | 7/1997 | Froehler et al. |
| 5,681,941 A | 10/1997 | Cook et al. |
| 5,698,685 A | 12/1997 | Summerton et al. |
| 5,750,692 A | 5/1998 | Cook et al. |
| 5,763,588 A | 6/1998 | Matteucci et al. |
| 5,801,154 A | 9/1998 | Baracchini et al. |
| 5,808,027 A | 9/1998 | Cook et al. |
| 5,811,534 A | 9/1998 | Cook et al. |
| 5,830,653 A | 11/1998 | Froehler et al. |
| 5,859,221 A | 1/1999 | Cook et al. |
| 5,948,903 A | 9/1999 | Cook et al. |

(Continued)

FOREIGN PATENT DOCUMENTS

| | | |
|---|---|---|
| WO | WO 1999/014226 | 3/1999 |
| WO | WO 2004/106356 | 12/2004 |

(Continued)

OTHER PUBLICATIONS

Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.
Braasch et al., "Novel Antisense and Peptide Nucleic Acid Strategies for Controlling Gene Expression" Biochemistry (2002) 41: 4503-4510.
Branch et al., "A good antisense molecule is hard to find," TIBS (1998) 23:45-50.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Crooke et al., "Basic Principles of Antisense Therapeutics" Antisense Research and Application (1998) Chapter 1:1-50.

(Continued)

Primary Examiner — Sean McGarry
(74) Attorney, Agent, or Firm — McNeill Baur PLLC

(57) ABSTRACT

The present embodiments provide methods, compounds, and compositions useful for inhibiting PMP22 expression and for treating, preventing, or ameliorating a disease associated with PMP22.

25 Claims, No Drawings
Specification includes a Sequence Listing.

(56) References Cited

U.S. PATENT DOCUMENTS

| | | | |
|---|---|---|---|
| 6,005,087 A | 12/1999 | Cook et al. |
| 6,005,096 A | 12/1999 | Matteucci et al. |
| 6,166,199 A | 12/2000 | Cook et al. |
| 6,268,490 B1 | 7/2001 | Imanishi et al. |
| 6,525,191 B1 | 2/2003 | Ramasamy |
| 6,531,584 B1 | 3/2003 | Cook et al. |
| 6,582,908 B2 | 6/2003 | Fodor et al. |
| 6,670,461 B1 | 12/2003 | Wengel et al. |
| 6,770,748 B2 | 8/2004 | Imanishi et al. |
| 6,794,499 B2 | 9/2004 | Wengel et al. |
| 7,034,133 B2 | 4/2006 | Wengel et al. |
| 7,053,207 B2 | 5/2006 | Wengel et al. |
| 7,399,845 B2 | 7/2008 | Seth et al. |
| 7,427,672 B2 | 9/2008 | Imanishi et al. |
| 7,547,684 B2 | 6/2009 | Seth et al. |
| 7,569,686 B1 | 8/2009 | Bhat et al. |
| 7,572,582 B2 | 8/2009 | Wengel et al. |
| 7,666,854 B2 | 2/2010 | Seth et al. |
| 7,696,345 B2 | 4/2010 | Allerson et al. |
| 7,741,457 B2 | 6/2010 | Swayze et al. |
| 7,750,131 B2 | 7/2010 | Seth et al. |
| 7,875,733 B2 | 1/2011 | Bhat et al. |
| 7,939,677 B2 | 5/2011 | Bhat et al. |
| 8,022,193 B2 | 9/2011 | Swayze et al. |
| 8,030,467 B2 | 10/2011 | Seth et al. |
| 8,034,909 B2 | 10/2011 | Wengel et al. |
| 8,080,644 B2 | 12/2011 | Wengel et al. |
| 8,088,746 B2 | 1/2012 | Seth et al. |
| 8,088,904 B2 | 1/2012 | Swayze et al. |
| 8,124,745 B2 | 2/2012 | Allerson et al. |
| 8,153,365 B2 | 4/2012 | Wengel et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,440,803 B2 | 5/2013 | Swayze et al. |
| 8,501,805 B2 | 8/2013 | Seth et al. |
| 8,530,640 B2 | 9/2013 | Seth et al. |
| 8,546,556 B2 | 10/2013 | Seth et al. |
| RE44,779 E | 2/2014 | Imanishi et al. |
| 8,796,437 B2 | 8/2014 | Swayze et al. |
| 9,005,906 B2 | 4/2015 | Swayze et al. |
| 9,012,421 B2 | 4/2015 | Migawa et al. |
| 2001/0053519 A1 | 12/2001 | Fodor et al. |
| 2003/0158403 A1 | 8/2003 | Manoharan et al. |
| 2003/0175906 A1 | 9/2003 | Manoharan et al. |
| 2003/0228597 A1 | 12/2003 | Cowsert et al. |
| 2007/0031844 A1 | 2/2007 | Khvorova et al. |
| 2008/0039618 A1 | 2/2008 | Allerson et al. |
| 2013/0197061 A1 | 8/2013 | Hohjoh et al. |
| 2013/0203836 A1 | 8/2013 | Rajeev et al. |
| 2014/0170162 A1 | 6/2014 | Gupta et al. |
| 2015/0157626 A1 | 6/2015 | Cohen et al. |
| 2015/0191727 A1 | 7/2015 | Migawa et al. |
| 2018/0066257 A1* | 3/2018 | Choi .................. A61K 31/713 |

FOREIGN PATENT DOCUMENTS

| | | |
|---|---|---|
| WO | WO 2007/134181 | 11/2007 |
| WO | WO 2008/101157 | 8/2008 |
| WO | WO 2008/113832 | 9/2008 |
| WO | WO 2009/068668 | 6/2009 |
| WO | WO 2011/133876 | 10/2011 |
| WO | WO 2014/179620 | 11/2014 |
| WO | WO 2015/106128 | 7/2015 |
| WO | WO 2017/029664 | 2/2017 |

OTHER PUBLICATIONS

Crooke et al., "Pharmacokinetic Properties of Several Novel Oligonucleotide Analogs in mice" J. Pharmacol. Exp. Ther. (1996) 277(2):923-937.

Crooke, ST., et al., "Antisense Drug Technology" Second Edition, CRC Press (2008) Chapters 1-28.

Englisch et al., "Chemically Modified Oligonucleotides as Probes and Inhibitors" Agnew Chem. Int. Ed. Engl. (1991) 30:613-629.

Freier et al., "The ups and downs of nucleic acid duplex stability: structure-stability studies on chemically-modified DNA:RNA duplexes" Nucleic Acids Research (1997) 25(22):4429-4443.

Frieden et al., "Expanding the design horizon of antisense oligonucleotides with alpha-L-LNA" Nucleic Acids Research (2003) 21: 6365-6372.

Genbank Accession No. NM_000304.3.

Genbank Accession No. NM_001302255.1.

Huxley et al., "Construction of a mouse model of Charcot-Marie-Tooth disease type 1A by pronuclear injection of human YAC DNA" Human Molecular Genetics (1996) 5: 563-569.

International Search Report for PCT/US2017/021534 dated May 31, 2017.

Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259:327.

Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.

Kroschwitz, "Polynucleotides" Concise Encyclopedia of Polymer Science and Engineering (1990) John Wiley & Sons, NY pp. 858-859.

Kumar et al., "The first analogues of LNA (locked nucleic acids): phosphorothioate-LNA and 2'-thio-LNA" Bioorg Med Chem Lett. (1998) 8:2219-2222.

Kumar et al., "Design, synthesis, biophysical and primer extension studies of novel acrylic butyl nucleic acid" Org. Biomol. Chem. (2013) 11: 5853-5865.

Lee et al., "Pmp22 mutant allele-specific siRNA alleviates demyelinating neuropathic phenotype in vivo" Neurobiol Dis (2017) 100: 99-107.

Letsinger et al., "Cholestelyl-conjugated oligonucleotides: Synthesis, properties, and activity as inhibitors of replication of human immunodeficiency virus in cell culture" PNAS (1989) 86:6553-6556.

Leumann, "DNA Analogues: From Supramolecular Principles to Biological Properties" Bioorg. & Med. Chem. (2002) 10: 841-854.

Manoharan et al., "Chemical Modifications to Improve Uptake and Bioavailability of Antisense Oligonucleotides" Ann. N.Y. Acad. Sci. (1992) 660: 306-309.

Manoharan et al., "Cholic Acid-Oligonucleotide Conjugates for Antisense Applications" Bioorg. Med. Chem. Lett. (1994) 4:1053-1060.

Manoharan et al., "Introduction of a Lipophilic Thioether Tether in the Minor Groove of Nucleic Acids for Antisense Applications" Bioorg. Med. Chem. Lett. (1993) 3(12):2765-2770.

Manoharan et al., "Lipidic Nucleic Acids" Tetrahedron Lett. (1995) 36(21):3651-3654.

Mishra et al., "Improved leishmanicidal effect of phosphorotioate antisense oligonucleotides by LDL-mediated delivery" Biochim. Biophys. Acta (1995) 1264:229-237.

New England Biolabs 1998/99 Catalog (cover page and pp. 121 and 284).

Nishina et al., "Chimeric Antisense Oligonucleotide Conjugated to α-Tocopherol" Molecular Therapy Nucleic Acids (2015) 4: e220.

Nishina et al., "Efficient In Vivo Delivery of siRNA to the Liver by Conjugation of α-Tocopherol" Molecular Therapy (2008) 16: 734-740.

Oberhauser et al., "Effective incorporation of 2'-O-methyl-oligoribonucleotides into liposomes and enhanced cell association through modifications with thiocholesterol" Nucl. Acids Res. (1992) 20(3):533-538.

Reynolds et al., "Rational siRNA design for RNA interference" Nature Biotechnology (2004) 22(3):326-330.

Saison-Behmoaras et al., "Short modified antisense oligonucleotides directed against Ha-ras point mutation induce selective cleavage of the mRNA and inhibit T24 cells proliferation" EMBO J. (1991) 10(5):1111-1118.

(56) References Cited

OTHER PUBLICATIONS

Sanghvi and P.D. Cook Eds. "Carbohydrate Modifications in Antisense Research" ACS Symposium Series 580; Chapters 3 and 4, (pp. 40-65).
Sanghvi et al., "Heterocyclic Base Modifications in Nucleic Acids and Their Applications in Antisense Oligonucleotides" Antisense Research and Applications (1993) pp. 273-288.
Shea et al., "Synthesis, hybridization properties and antiviral activity of lipid-oligodeoxynucleotide conjugates" Nucl. Acids Res. (1990) 18(13):3777-3783.
Singh et al., "LNA (locked nucleic acids): synthesis and high-affinity nucleic acid recognition" Chem. Commun. (1998) 455-456.
Singh et al., "Synthesis of 2'-amino-LNA: a novel conformationally restricted high-affinity oligonucleotide analogue with a handle" J. Org. Chem. (1998) 63: 10035-10039.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.
Svinarchuk et al., "Inhibition of HIV proliferation in MT-4 cells by antisense oligonucleotide conjugated to lipophilic groups" Biochimie (1993) 75:49-54.
Verhamme et al., "Myelin and axon pathology in a long-term study of PMP22-overexpressing mice" *Journal of Neuropathology and Experimental Neurology* (2011) 70: 386-398.
Young et al., "Medical treatment of hereditary neuropathies" Hereditary Peripheral Neuropathies (2005) 199-205.
Zhou et al., "Fine tuning of electrostatics around the internucleotidic phosphate through incorporation of modified 2',4'-carbocyclic-LNAs and- ENAs leads to significant modulation of antisense properties" *J. Org. Chem.* (2009) 74: 118-134.
Extended EP Search Report for 17764073.7 dated Nov. 28, 2019.
Hai et al., "Competitive binding of triplex-forming oligonucleotides in the two alternate promoters of the PMP22 gene" Antisense Nucleic Acid Drug Dev (2001) 11: 233-246.
Kovach et al., "A unique point mutation in the PMP22 gene is associated with Charcot-Marie-Tooth disease and deafness" Am J Hum Genet (1999) 64: 1580-1593.
Patzko et al., "Update on Charcot-Marie-Tooth disease" Curr Neurol Neurosci Rep (2011) 11: 78-88.
Tanaka et al., "Mouse models of Charcot-Marie-Tooth disease" Trends Genet (2002) 18: S39-S44.
Zhao et al., "PMP22 antisense oligonucleotides reverse Charcot-Marie-Tooth disease type 1A features in rodent models" J Clin Invest (2018) 128: 359-368.

\* cited by examiner

METHODS AND COMPOSITIONS FOR INHIBITING PMP22 EXPRESSION

SEQUENCE LISTING

The present application is being filed along with a Sequence Listing in electronic format. The Sequence Listing is provided as a file entitled BIOL0287USASEQ_ST25.txt created Aug. 28, 2018, which is 8 kb in size. The information in the electronic format of the sequence listing is incorporated herein by reference in its entirety.

FIELD

The present embodiments provide methods, compounds, and compositions useful for inhibiting PMP22 expression, which can be useful for treating, preventing, or ameliorating a disease associated with PMP22.

BACKGROUND

Charcot-Marie-Tooth Disease (CMT) is a neurological disorder that affects motor and sensory nerve function. Typical symptoms include muscle weakness in the feet and lower legs, foot deformities, and mild to severe pain. There is no cure for CMT, and treatment typically includes physical therapy, occupational therapy, use of braces, and/or use of pharmaceuticals for pain relief. Several inherited genetic mutations are associated with CMT. For example, duplication of Peripheral Myelin Protein 22 (PMP22) is associated with CMT, specifically CMT Type 1A.

SUMMARY

In certain embodiments, the present disclosure provides methods of treating a disease associated with PMP22, such as Charcot-Marie-Tooth Disease. In certain embodiments, the present disclosure provides methods of inhibiting a PMP22 transcript in a nerve cell. In certain such embodiments, the nerve cell is a Schwann cell. In certain embodiments, the methods provided herein increase compound muscle action potential and/or motor nerve conduction velocity.

In certain embodiments, the present disclosure provides compound comprising oligonucleotides. In certain such embodiments, the compounds are oligomeric compounds. In certain embodiments, the oligonucleotides are complementary to a target region of a PMP22 transcript. Certain embodiments provided herein are directed to compounds and compositions useful for inhibiting PMP22 expression, which can be useful for treating, preventing, ameliorating, or slowing progression of Charcot-Marie-Tooth Disease. The present disclosure provides the following non-limiting numbered embodiments:

Embodiment 1. A method of treating, preventing, or ameliorating Charcot-Marie-Tooth Disease in an individual comprising administering to the individual an oligomeric compound comprising a modified oligonucleotide, and thereby treating, preventing, or ameliorating Charcot-Marie-Tooth Disease.

Embodiment 2. A method of treating, preventing, or ameliorating a disease associated with PMP22 in an individual comprising administering to the individual an oligomeric compound comprising a modified oligonucleotide, and thereby treating, preventing, or ameliorating the disease.

Embodiment 3. A method comprising administering an oligomeric compound comprising a modified oligonucleotide to an individual for treating, preventing, or ameliorating Charcot-Marie-Tooth Disease, and thereby treating, preventing, or ameliorating Charcot-Marie-Tooth Disease.

Embodiment 4. A method comprising administering an oligomeric compound comprising a modified oligonucleotide to an individual for treating, preventing, or ameliorating a disease associated with PMP22, and thereby treating, preventing, or ameliorating the disease.

Embodiment 5. A method of reducing the amount or activity of a PMP22 transcript in a nerve of an individual having, or at risk of having, a disease associated with PMP22 comprising administering an oligomeric compound comprising a modified oligonucleotide, and thereby reducing the amount or activity of a PMP22 transcript in the nerve of the individual.

Embodiment 6. The method of embodiment 5, wherein the amount or activity of a PMP22 transcript is reduced in Schwann cells of the individual.

Embodiment 7. The method of any of embodiments 1-6, wherein the individual exhibits at least one symptom of Charcot-Marie-Tooth Disease.

Embodiment 8. The method of any of embodiments 1-7, wherein the individual is a mammal.

Embodiment 9. The method of any of embodiments 1-7, wherein the individual is a human.

Embodiment 10. Use of an oligomeric compound comprising a modified oligonucleotide for treating, preventing, or ameliorating Charcot-Marie-Tooth Disease.

Embodiment 11. Use of an oligomeric compound comprising a modified oligonucleotide for treating, preventing, or ameliorating a disease associated with PMP22.

Embodiment 12. Use of an oligomeric compound comprising a modified oligonucleotide for the manufacture of a medicament for treating, preventing, or ameliorating Charcot-Marie-Tooth Disease.

Embodiment 13. Use of an oligomeric compound comprising a modified oligonucleotide for the manufacture of a medicament for treating, preventing, or ameliorating a disease associated with PMP22.

Embodiment 14. Use of an oligomeric compound comprising a modified oligonucleotide for the preparation of a medicament for treating, preventing, or ameliorating Charcot-Marie-Tooth Disease.

Embodiment 15. Use of an oligomeric compound comprising a modified oligonucleotide for the preparation of a medicament for treating, preventing, or ameliorating a disease associated with PMP22.

Embodiment 16. The method or use of any of embodiments 1-15, wherein the oligomeric compound is a pharmaceutically acceptable salt.

Embodiment 17. The method or use of any of embodiments 1-16, wherein the oligomeric compound is administered in a pharmaceutically acceptable carrier or diluent.

Embodiment 18. The method or use of any of embodiments 1-17, wherein the disease is Charcot-Marie-Tooth Disease Type 1.

Embodiment 19. The method or use of any of embodiments 1-18, wherein the disease is Charcot-Marie-Tooth Disease Type 1A.

Embodiment 20. The method or use of any of embodiments 1-19, wherein the oligomeric compound is administered systemically.

Embodiment 21. The method or use of any of embodiments 1-20, wherein the oligomeric compound is administered subcutaneously.

Embodiment 22. The method or use of any of embodiments 1-21, wherein motor nerve conduction velocity is increased.

Embodiment 23. The method or use of any of embodiments 1-22, wherein oligomeric compound muscle action potential is increased.

Embodiment 24. The method or use of any of embodiments 1-23, wherein grip strength is increased.

Embodiment 25. The method or use of any of embodiments 1-24, wherein myelination of a nerve is increased.

Embodiment 26. The method or use of any of embodiments 1-25, wherein at least one symptom of the disease is alleviated.

Embodiment 27. The method or use of any of embodiments 1-26, wherein the rate of progression of at least one symptom of the disease is decreased.

Embodiment 28. The method or use of any of embodiments 1-27, wherein the modified oligonucleotide comprises a complementary region of at least 10 contiguous nucleobases, wherein the nucleobase sequence of the complementary region is complementary to a target region of a PMP22 transcript.

Embodiment 29. The method or use of embodiment 28, wherein the complementary region is at least 12 contiguous nucleobases.

Embodiment 30. The method or use of embodiment 28, wherein the complementary region is at least 14 contiguous nucleobases.

Embodiment 31. The method or use of embodiment 28, wherein the complementary region is at least 16 contiguous nucleobases.

Embodiment 32. The method or use of embodiment 28, wherein the complementary region is at least 20 contiguous nucleobases.

Embodiment 33. The method or use of any of embodiments 1-27, wherein the nucleobase sequence of the modified oligonucleotide is at least 80% complementary to a target region of a PMP22 transcript.

Embodiment 34. The method or use of embodiment 33, wherein the nucleobase sequence of the modified oligonucleotide is at least 85% complementary to the target region of the PMP22 transcript.

Embodiment 35. The method or use of embodiment 33, wherein the nucleobase sequence of the modified oligonucleotide is at least 90% complementary to the target region of the PMP22 transcript.

Embodiment 36. The method or use of embodiment 33, wherein the nucleobase sequence of the modified oligonucleotide is at least 95% complementary to the target region of the PMP22 transcript.

Embodiment 37. The method or use of embodiment 33, wherein the nucleobase sequence of the modified oligonucleotide is 100% complementary to the target region of the PMP22 transcript.

Embodiment 38. The method or use of any of embodiments 28-37, wherein the PMP22 transcript is a PMP22 pre-mRNA.

Embodiment 39. The method or use of any of embodiments 28-37, wherein the PMP22 transcript is a PMP22 mRNA.

Embodiment 40. The method or use of any of embodiments 28-37, wherein the PMP22 transcript is SEQ ID NO: 1.

Embodiment 41. The method or use of any of embodiments 1-40, wherein the modified oligonucleotide comprises SEQ ID NO: 16.

Embodiment 42. The method or use of any of embodiments 1-41, wherein the modified oligonucleotide comprises at least one modified nucleoside.

Embodiment 43. The method or use of embodiment 42, wherein at least one modified nucleoside comprises a modified sugar moiety.

Embodiment 44. The method or use of embodiment 43, wherein at least one modified sugar moiety is a non-bicyclic, 2'-substituted sugar moiety.

Embodiment 45. The method or use of embodiment 44, wherein the non-bicyclic, 2'-substituted sugar moiety is selected from among: 2'-OMe, 2'-F, and 2'-MOE.

Embodiment 46. The method or use of embodiment 45, wherein the non-bicyclic, 2'-substituted sugar moiety is 2'-MOE.

Embodiment 47. The method or use of embodiments 43-46, wherein at least one modified sugar moiety is a bicyclic sugar moiety.

Embodiment 48. The method or use of embodiment 47, wherein at least one bicyclic sugar moiety is LNA or cEt.

Embodiment 49. The method or use of embodiment 43, wherein at least one sugar moiety is a sugar surrogate.

Embodiment 50. The method or use of embodiment 49, wherein at least one sugar surrogate is a morpholino.

Embodiment 51. The method or use of embodiment 50, wherein at least one sugar surrogate is a modified morpholino.

Embodiment 52. The method or use of any of embodiments 42-49, wherein the modified oligonucleotide comprises:
a gap segment consisting of linked 2'-deoxynucleosides;
a 5' wing segment consisting of linked nucleosides; and
a 3' wing segment consisting of linked nucleosides;
wherein the gap segment is positioned between the 5' wing segment and the 3' wing segment, and
wherein the 3' most nucleoside of the 5' wing and the 5' most nucleoside of the 3' wing each comprises a modified sugar.

Embodiment 53. The method or use of embodiment 52, wherein each nucleoside of the 5' wing segment and each nucleoside of the 3' wing segment comprises a modified sugar.

Embodiment 54. The method or use of any of embodiments 52-53, wherein at least two of the modified sugar moieties are different from each other.

Embodiment 55. The method or use of any of embodiments 52-53, wherein all of the modified sugar moieties are the same as each other.

Embodiment 56. The method or use of embodiment 55, wherein the modified sugar moieties are non-bicyclic sugar moieties.

Embodiment 57. The method or use of embodiment 56, wherein the non-bicyclic sugar moieties are 2'-OMe, 2'-F, or 2'-MOE.

Embodiment 58. The method or use of embodiment 55, wherein the modified sugar moieties are bicyclic sugar moieties.

Embodiment 59. The method or use of embodiment 58, wherein the modified sugar moieties are LNA or cEt.

Embodiment 60. The method or use of embodiment 59, wherein the modified sugar moieties are cEt.

Embodiment 61. The method or use of any of embodiments 1-60, wherein the modified oligonucleotide comprises 16 linked nucleosides.

Embodiment 62. The method or use of any of embodiments 1-60, wherein the modified oligonucleotide consists of 16 linked nucleosides.

Embodiment 63. The method or use of any of embodiments 1-62, wherein the oligomeric compound comprises a conjugate group.

Embodiment 64. The method or use of any of embodiments 1-63, wherein the modified oligonucleotide comprises at least one modified internucleoside linkage.

Embodiment 65. The method or use of embodiment 64, wherein each internucleoside linkage of the modified oligonucleotide is a modified internucleoside linkage.

Embodiment 66. The method or use of any of embodiments 64-65, wherein at least one modified internucleoside linkage is a phosphorothioate internucleoside linkage.

Embodiment 67. The method or use of any of embodiments 64-66, wherein each internucleoside linkage is a modified internucleoside linkage and wherein each internucleoside linkage comprises the same modification.

Embodiment 68. The method or use of embodiment 67, wherein each internucleoside linkage is a phosphorothioate internucleoside linkage.

Embodiment 69. The method or use of any of embodiments 1-68, wherein the oligomeric compound is an RNase H based antisense compound.

Embodiment 70. The method or use of any of embodiments 1-68, wherein the oligomeric compound is an RNAi antisense compound.

Embodiment 71. The method or use of any of embodiments 1-70, wherein the oligomeric compound is single-stranded.

Embodiment 72. The method or use of any of embodiments 1-70, wherein the oligomeric compound is paired with a second oligomeric compound to form a duplex.

Embodiment 73. The method or use of embodiment 72, wherein the second oligomeric compound comprises an oligonucleotide and a conjugate group.

Embodiment 74. A method of reducing PMP22 expression in a cell comprising contacting the cell with an oligomeric compound comprising a modified oligonucleotide, wherein the cell is a nerve cell.

Embodiment 75. The method of embodiment 74, wherein the nerve cell is a Schwann cell.

Embodiment 76. A method of increasing compound muscle action potential of a nerve, comprising contacting a cell with an oligomeric compound comprising a modified oligonucleotide.

Embodiment 77. The method of any of embodiments 74-76, wherein the cell is in an animal.

Embodiment 78. The method of embodiment 77, wherein the animal is a mouse.

Embodiment 79. The method of embodiment 77, wherein the animal is a human.

Embodiment 80. The method of any of embodiments 74-79, wherein the oligomeric compound is a pharmaceutically acceptable salt.

Embodiment 81. The method of any of embodiments 74-80, wherein the oligomeric compound is administered in a pharmaceutically acceptable carrier or diluent.

Embodiment 82. The method of any of embodiments 74-81, wherein the modified oligonucleotide comprises a complementary region of at least 10 contiguous nucleobases, wherein the nucleobase sequence of the complementary region is complementary to a target region of a PMP22 transcript.

Embodiment 83. The method of embodiment 82, wherein the complementary region is at least 12 contiguous nucleobases.

Embodiment 84. The method of embodiment 82, wherein the complementary region is at least 14 contiguous nucleobases.

Embodiment 85. The method of embodiment 82, wherein the complementary region is at least 16 contiguous nucleobases.

Embodiment 86. The method of embodiment 82, wherein the complementary region is at least 20 contiguous nucleobases.

Embodiment 87. The method of any of embodiments 74-81, wherein the nucleobase sequence of the modified oligonucleotide is at least 80% complementary to a target region of a PMP22 transcript.

Embodiment 88. The method of embodiment 87, wherein the nucleobase sequence of the modified oligonucleotide is at least 85% complementary to the target region of the PMP22 transcript.

Embodiment 89. The method of embodiment 87, wherein the nucleobase sequence of the modified oligonucleotide is at least 90% complementary to the target region of the PMP22 transcript.

Embodiment 90. The method of embodiment 87, wherein the nucleobase sequence of the modified oligonucleotide is at least 95% complementary to the target region of the PMP22 transcript.

Embodiment 91. The method of embodiment 87, wherein the nucleobase sequence of the modified oligonucleotide is 100% complementary to the target region of the PMP22 transcript.

Embodiment 92. The method of any of embodiments 82-91, wherein the PMP22 transcript is a PMP22 pre-mRNA.

Embodiment 93. The method of any of embodiments 82-91, wherein the PMP22 transcript is a PMP22 mRNA.

Embodiment 94. The method of any of embodiments 82-91, wherein the PMP22 transcript is SEQ ID NO: 1.

Embodiment 95. The method of any of embodiments 74-94, wherein the modified oligonucleotide comprises SEQ ID NO: 16.

Embodiment 96. The method of any of embodiments 74-95, wherein the modified oligonucleotide comprises at least one modified nucleoside.

Embodiment 97. The method of embodiment 96, wherein at least one modified nucleoside comprises a modified sugar moiety.

Embodiment 98. The method of embodiment 97, wherein at least one modified sugar moiety is a non-bicyclic, 2'-substituted sugar moiety.

Embodiment 99. The method of embodiment 98, wherein the non-bicyclic, 2'-substituted sugar moiety is selected from among: 2'-OMe, 2'-F, and 2'-MOE.

Embodiment 100. The method of embodiment 99, wherein the non-bicyclic, 2'-substituted sugar moiety is 2'-MOE.

Embodiment 101. The method of embodiments 97-100, wherein at least one modified sugar moiety is a bicyclic sugar moiety.

Embodiment 102. The method of embodiment 101, wherein at least one bicyclic sugar moiety is LNA or cEt.

Embodiment 103. The method of embodiment 97, wherein at least one sugar moiety is a sugar surrogate.

Embodiment 104. The method of embodiment 103, wherein at least one sugar surrogate is a morpholino.

Embodiment 105. The method of embodiment 103, wherein at least one sugar surrogate is a modified morpholino.

Embodiment 106. The method of any of embodiments 74-103, wherein the modified oligonucleotide comprises:
a gap segment consisting of linked 2'-deoxynucleosides;
a 5' wing segment consisting of linked nucleosides; and
a 3' wing segment consisting of linked nucleosides;
wherein the gap segment is positioned between the 5' wing segment and the 3' wing segment, and
wherein the 3' most nucleoside of the 5' wing and the 5' most nucleoside of the 3' wing each comprises a modified sugar.

Embodiment 107. The method of embodiment 106, wherein each nucleoside of the 5' wing segment and each nucleoside of the 3' wing segment comprises a modified sugar.

Embodiment 108. The method of any of embodiments 106-107, wherein at least two of the modified sugar moieties are different from each other.

Embodiment 109. The method of any of embodiments 106-107, wherein all of the modified sugar moieties are the same as each other.

Embodiment 110. The method of embodiment 109, wherein the modified sugar moieties are non-bicyclic sugar moieties.

Embodiment 111. The method of embodiment 110, wherein the non-bicyclic sugar moieties are 2'-OMe, 2'-F, or 2'-MOE.

Embodiment 112. The method of embodiment 109, wherein the modified sugar moieties are bicyclic sugar moieties.

Embodiment 113. The method of embodiment 112, wherein the modified sugar moieties are LNA or cEt.

Embodiment 114. The method of embodiment 113, wherein the modified sugar moieties are cEt.

Embodiment 115. The method of any of embodiments 74-114, wherein the modified oligonucleotide comprises 16 linked nucleosides.

Embodiment 116. The method of any of embodiments 74-114, wherein the modified oligonucleotide consists of 16 linked nucleosides.

Embodiment 117. The method of any of embodiments 74-116, wherein the oligomeric compound comprises a conjugate group.

Embodiment 118. The method of any of embodiments 74-117, wherein the modified oligonucleotide comprises at least one modified internucleoside linkage.

Embodiment 119. The method of embodiment 118, wherein each internucleoside linkage of the modified oligonucleotide is a modified internucleoside linkage.

Embodiment 120. The method of any of embodiments 118-119, wherein at least one modified internucleoside linkage is a phosphorothioate internucleoside linkage.

Embodiment 121. The method of any of embodiments 118-120, wherein each internucleoside linkage is a modified internucleoside linkage and wherein each internucleoside linkage comprises the same modification.

Embodiment 122. The method of embodiment 121, wherein each internucleoside linkage is a phosphorothioate internucleoside linkage.

Embodiment 123. The method of any of embodiments 74-122, wherein the oligomeric compound is an RNase H based antisense compound.

Embodiment 124. The method of any of embodiments 74-122, wherein the oligomeric compound is an RNAi antisense compound.

Embodiment 125. The method of any of embodiments 74-124, wherein the oligomeric compound is single-stranded.

Embodiment 126. The method of any of embodiments 74-124, wherein the oligomeric compound is paired with a second oligomeric compound to form a duplex.

Embodiment 127. The method of embodiment 126, wherein the second oligomeric compound comprises an oligonucleotide and a conjugate group.

Embodiment 128. A compound comprising a modified oligonucleotide, wherein the modified oligonucleotide comprises SEQ ID NO: 16.

Embodiment 129. A compound comprising a modified oligonucleotide, wherein the nucleobase sequence of the modified oligonucleotide consists of SEQ ID NO: 16.

Embodiment 130. The compound of any of embodiments 128-129, wherein the modified oligonucleotide comprises at least one modified nucleoside.

Embodiment 131. The compound of embodiment 130, wherein the modified nucleoside comprises a cEt bicyclic sugar moiety.

Embodiment 132. The compound of any of embodiments 128-131, wherein the modified nucleotide comprises a phosphorothioate internucleoside linkage.

Embodiment 133. The compound of any of embodiments 128-132, wherein the compound is an oligomeric compound.

Embodiment 134. The compound of any of embodiments 128-133, wherein the modified oligonucleotide consists of Isis No. 684267.

Embodiment 135. The compound of any of embodiments 128-134, wherein the compound consists of Isis No. 684267.

Embodiment 136. The compound of embodiment 134 or 135, wherein the modified oligonucleotide is a salt.

Embodiment 137. The compound of embodiment 134 or 135, wherein the modified oligonucleotide is a sodium salt.

Embodiment 138. A compound comprising a modified oligonucleotide, wherein the modified oligonucleotide comprises SEQ ID NO: 10.

Embodiment 139. A compound comprising a modified oligonucleotide, wherein the nucleobase sequence of the modified oligonucleotide consists of SEQ ID NO: 10.

Embodiment 140. A compound comprising a modified oligonucleotide, wherein the modified oligonucleotide comprises SEQ ID NO: 14.

Embodiment 141. A compound comprising a modified oligonucleotide, wherein the nucleobase sequence of the modified oligonucleotide consists of SEQ ID NO: 14.

Embodiment 142. The compound of any of embodiments 138-141, wherein the modified oligonucleotide comprises at least one modified nucleoside.

Embodiment 143. The compound of embodiment 142, wherein the modified nucleoside comprises a cEt bicyclic sugar moiety.

Embodiment 144. The compound of any of embodiments 138-143, wherein the modified nucleotide comprises a phosphorothioate internucleoside linkage.

Embodiment 145. The compound of any of embodiments 138-144, wherein the compound is an oligomeric compound.

Embodiment 146. The compound of any of embodiments 138-145, wherein the modified oligonucleotide consists of Isis No. 684934.

Embodiment 147. The compound of any of embodiments 138-146, wherein the modified oligonucleotide consists of Isis No. 718292.

Embodiment 148. A pharmaceutical composition comprising the modified oligonucleotide of embodiment 146 or 147 and at least one pharmaceutically acceptable carrier or diluent.

Embodiment 149. The modified oligonucleotide of embodiment 146 or 147, wherein the modified oligonucleotide is a salt.

Embodiment 150. The modified oligonucleotide of embodiment 146 or 147, wherein the modified oligonucleotide is a sodium salt.

DETAILED DESCRIPTION

It is to be understood that both the foregoing general description and the following detailed description are exemplary and explanatory only and are not restrictive. Herein, the use of the term "including" as well as other forms, such as "includes" and "included", is not limiting.

The section headings used herein are for organizational purposes only and are not to be construed as limiting the subject matter described. All documents, or portions of documents, cited in this application, including, but not limited to, patents, patent applications, articles, books, treatises, and GenBank and NCBI reference sequence records are hereby expressly incorporated by reference for the portions of the document discussed herein, as well as in their entirety.

It is understood that the sequence set forth in each sequence ID Number (SEQ ID NO.) herein is independent of any modification to a sugar moiety, an internucleoside linkage, or a nucleobase. As such, oligonucleotides defined by a SEQ ID NO. may comprise, independently, one or more modifications to a sugar moiety, an internucleoside linkage, or a nucleobase.

As used herein, "2'-deoxynucleoside" means a nucleoside comprising 2'-H(H) furanosyl sugar moiety, as found in naturally occurring deoxyribonucleic acids (DNA). In certain embodiments, a 2'-deoxynucleoside may comprise a modified nucleobase or may comprise an RNA nucleobase (uracil).

As used herein, "2'-substituted nucleoside" or "2-modified nucleoside" means a nucleoside comprising a 2'-substituted or 2'-modified sugar moiety. As used herein, "2'-substituted" or "2-modified" in reference to a sugar moiety means a sugar moiety comprising at least one 2'-substituent group other than H or OH.

As used herein, "antisense activity" means any detectable and/or measurable change attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound.

As used herein, "antisense compound" means a compound comprising an antisense oligonucleotide and optionally one or more additional features, such as a conjugate group or terminal group. As used herein, "antisense oligonucleotide" means an oligonucleotide having a nucleobase sequence that is at least partially complementary to a target nucleic acid.

As used herein, "amelioration" refers to an improvement or lessening of at least one indicator, sign, or symptom of an associated disease, disorder, or condition. In certain embodiments, amelioration includes a delay or slowing in the progression or severity of one or more indicators of a condition or disease. The progression or severity of indicators may be determined by subjective or objective measures, which are known to those skilled in the art.

As used herein, "ameliorate" in reference to a treatment means improvement in at least one symptom relative to the same symptom in the absence of the treatment. In certain embodiments, amelioration is the reduction in the severity or frequency of a symptom or the delayed onset or slowing of progression in the severity or frequency of a symptom.

As used herein, "bicyclic nucleoside" or "BNA" means a nucleoside comprising a bicyclic sugar moiety. As used herein, "bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

As used herein, "branching group" means a group of atoms having at least 3 positions that are capable of forming covalent linkages to at least 3 groups. In certain embodiments, a branching group provides a plurality of reactive sites for connecting tethered ligands to an oligonucleotide via a conjugate linker and/or a cleavable moiety.

As used herein, "cell-targeting moiety" means a conjugate group or portion of a conjugate group that is capable of binding to a particular cell type or particular cell types.

As used herein, "cleavable moiety" means a bond or group of atoms that is cleaved under physiological conditions, for example, inside a cell, an animal, or a human.

As used herein, "complementary" in reference to an oligonucleotide means that at least 70% of the nucleobases of such oligonucleotide or one or more regions thereof and the nucleobases of another nucleic acid or one or more regions thereof are capable of hydrogen bonding with one another when the nucleobase sequence of the oligonucleotide and the other nucleic acid are aligned in opposing directions. Complementary nucleobases means nucleobases that are capable of forming hydrogen bonds with one another.

Complementary nucleobase pairs include adenine (A) and thymine (T), adenine (A) and uracil (U), cytosine (C) and guanine (G), 5-methyl cytosine ($^m$C) and guanine (G). Complementary oligonucleotides and/or nucleic acids need not have nucleobase complementarity at each nucleoside. Rather, some mismatches are tolerated. As used herein, "fully complementary" or "100% complementary" in reference to oligonucleotides means that such oligonucleotides are complementary to another oligonucleotide or nucleic acid at each nucleoside of the oligonucleotide.

As used herein, "conjugate group" means a group of atoms that is directly or indirectly attached to an oligonucleotide. Conjugate groups include a conjugate moiety and a conjugate linker that attaches the conjugate moiety to the oligonucleotide.

As used herein, "conjugate linker" means a group of atoms comprising at least one bond that connects a conjugate moiety to an oligonucleotide.

As used herein, "conjugate moiety" means a group of atoms that is attached to an oligonucleotide via a conjugate linker.

As used herein, "contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

As used herein, "decrease" means lower to a smaller extent, size, amount, or number.

As used herein, "double-stranded antisense compound" means an antisense compound comprising two oligomeric compounds that are complementary to each other and form a duplex, and wherein one of the two said oligomeric compounds comprises an antisense oligonucleotide.

As used herein, "fully modified" in reference to a modified oligonucleotide means a modified oligonucleotide in which each sugar moiety is modified. "Uniformly modified" in reference to a modified oligonucleotide means a fully modified oligonucleotide in which each sugar moiety is the same. For example, the nucleosides of a uniformly modified oligonucleotide can each have a 2'-MOE modification but different nucleobase modifications, and the internucleoside linkages may be different.

As used herein, "gapmer" means an antisense oligonucleotide comprising an internal region having a plurality of nucleosides that support RNase H cleavage positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

As used herein, "hybridization" means the pairing or annealing of complementary oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases.

As used herein, "increase" means raise to a larger extent, size, amount, or number.

As used herein, "individual" means a human or non-human animal selected for treatment or therapy.

As used herein, "inhibiting" in reference to expression, amount, or activity refers to a reduction or blockade of the expression, amount, or activity relative to the expression, amount, or activity in an untreated or control sample and does not necessarily indicate a total elimination of expression, amount, or activity.

As used herein, the terms "internucleoside linkage" means a group or bond that forms a covalent linkage between adjacent nucleosides in an oligonucleotide. As used herein "modified internucleoside linkage" means any internucleoside linkage other than a naturally occurring, phosphate internucleoside linkage. Non-phosphate linkages are referred to herein as modified internucleoside linkages. "Phosphorothioate linkage" means a modified phosphate linkage in which one of the non-bridging oxygen atoms is replaced with a sulfur atom. A phosphorothioate internucleoside linkage is a modified internucleoside linkage. Modified internucleoside linkages include linkages that comprise abasic nucleosides. As used herein, "abasic nucleoside" means a sugar moiety in an oligonucleotide or oligomeric compound that is not directly connected to a nucleobase. In certain embodiments, an abasic nucleoside is adjacent to one or two nucleosides in an oligonucleotide.

As used herein, "linker-nucleoside" means a nucleoside that links, either directly or indirectly, an oligonucleotide to a conjugate moiety. Linker-nucleosides are located within the conjugate linker of an oligomeric compound. Linker-nucleosides are not considered part of the oligonucleotide portion of an oligomeric compound even if they are contiguous with the oligonucleotide.

As used herein, "non-bicyclic modified sugar" or "non-bicyclic modified sugar moiety" means a modified sugar moiety that comprises a modification, such as a substitutent, that does not form a bridge between two atoms of the sugar to form a second ring.

As used herein, "linked nucleosides" are nucleosides that are connected in a continuous sequence (i.e. no additional nucleosides are present between those that are linked).

As used herein, "mismatch" or "non-complementary" means a nucleobase of a first oligonucleotide that is not complementary with the corresponding nucleobase of a second oligonucleotide or target nucleic acid when the first and second oligomeric compound are aligned.

As used herein, "MOE" means methoxyethyl. "2'-MOE" means a —OCH$_2$CH$_2$OCH$_3$ group at the 2' position of a furanosyl ring.

As used herein, "motif" means the pattern of unmodified and/or modified sugar moieties, nucleobases, and/or internucleoside linkages, in an oligonucleotide. As used herein, "naturally occurring" means found in nature.

As used herein, "nucleobase" means a naturally occurring nucleobase or a modified nucleobase. As used herein a "naturally occurring nucleobase" is adenine (A), thymine (T), cytosine (C), uracil (U), and guanine (G). As used herein, a modified nucleobase is a group of atoms capable of pairing with at least one naturally occurring nucleobase. A universal base is a nucleobase that can pair with any one of the five unmodified nucleobases. As used herein, "nucleobase sequence" means the order of contiguous nucleobases in a nucleic acid or oligonucleotide independent of any sugar or internucleoside linkage modification.

As used herein, "nucleoside" means a compound comprising a nucleobase and a sugar moiety. The nucleobase and sugar moiety are each, independently, unmodified or modified. As used herein, "modified nucleoside" means a nucleoside comprising a modified nucleobase and/or a modified sugar moiety.

As used herein, "oligomeric compound" means a compound consisting of an oligonucleotide and optionally one or more additional features, such as a conjugate group or terminal group.

As used herein, "oligonucleotide" means a strand of linked nucleosides connected via internucleoside linkages, wherein each nucleoside and internucleoside linkage may be modified or unmodified. Unless otherwise indicated, oligonucleotides consist of 8-50 linked nucleosides. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

As used herein, "Peripheral Myelin Protein 22" or "PMP22" means a nucleic acid that encodes PMP22 or a PMP22 protein. For example, in certain embodiments, PMP22 nucleic acids include a DNA sequence encoding PMP22, and an RNA sequence transcribed from a DNA encoding PMP22 (e.g., a PMP22 transcript). As used herein, a "PMP22 transcript" is an RNA that is transcribed from a DNA encoding PMP22 and itself codes for a PMP22 protein. In certain embodiments, a PMP22 transcript is a PMP22 pre-mRNA. In certain embodiments, a PMP22 transcript is a PMP22 mRNA.

As used herein, "pharmaceutically acceptable carrier or diluent" means any substance suitable for use in administering to an animal Certain such carriers enable pharmaceutical compositions to be formulated as, for example, tablets, pills, dragees, capsules, liquids, gels, syrups, slurries, suspension and lozenges for the oral ingestion by a subject. In certain embodiments, a pharmaceutically acceptable carrier or diluent is sterile water; sterile saline; or sterile buffer solution.

As used herein "pharmaceutically acceptable salts" means physiologically and pharmaceutically acceptable salts of compounds, such as oligomeric compounds, i.e., salts that retain the desired biological activity of the parent compound and do not impart undesired toxicological effects thereto.

As used herein "pharmaceutical composition" means a mixture of substances suitable for administering to a subject. For example, a pharmaceutical composition may comprise an antisense compound and a sterile aqueous solution. In certain embodiments, a pharmaceutical composition shows activity in free uptake assay in certain cell lines.

As used herein, "phosphorus moiety" means a group of atoms comprising a phosphorus atom. In certain embodiments, a phosphorus moiety comprises a mono-, di-, or tri-phosphate, or phosphorothioate.

As used herein "prodrug" means a therapeutic agent in a form outside the body that is converted to a different form within the body or cells thereof. Typically conversion of a prodrug within the body is facilitated by the action of an enzymes (e.g., endogenous or viral enzyme) or chemicals present in cells or tissues and/or by physiologic conditions.

As used herein, "RNAi compound" means an antisense compound that acts, at least in part, through RISC or Ago2 to modulate a target nucleic acid and/or protein encoded by a target nucleic acid. RNAi compounds include, but are not limited to double-stranded siRNA, single-stranded RNA (ssRNA), and microRNA, including microRNA mimics. In certain embodiments, an RNAi compound modulates the amount, activity, and/or splicing of a target nucleic acid. The term RNAi compound excludes antisense oligonucleotides that act through RNase H.

As used herein, the term "single-stranded" in reference to a compound means such a compound consisting of one oligomeric compound that is not paired with a second oligomeric compound to form a duplex. "Self-complementary" in reference to an oligonucleotide means an oligonucleotide that at least partially hybridizes to itself. A compound consisting of one oligomeric compound, wherein the oligonucleotide of the oligomeric compound is self-complementary, is a single-stranded compound. A single-stranded antisense or oligomeric compound may be capable of binding to a complementary oligomeric compound to form a duplex.

As used herein, "standard in vivo experiment" means the procedure described in Example 1 and reasonable variations thereof.

As used herein, "sugar moiety" means an unmodified sugar moiety or a modified sugar moiety. As used herein, "unmodified sugar moiety" means a 2'-OH(H) furanosyl moiety, as found in RNA (an "unmodified RNA sugar moiety"), or a 2'-H(H) moiety, as found in DNA (an "unmodified DNA sugar moiety"). Unmodified sugar moieties have one hydrogen at each of the 1', 3', and 4' positions, an oxygen at the 3' position, and two hydrogens at the 5' position. As used herein, "modified sugar moiety" or "modified sugar" means a modified furanosyl sugar moiety or a sugar surrogate. As used herein, modified furanosyl sugar moiety means a furanosyl sugar comprising a non-hydrogen substituent in place of at least one hydrogen of an unmodified sugar moiety. In certain embodiments, a modified furanosyl sugar moiety is a 2'-substituted sugar moiety. Such modified furanosyl sugar moieties include bicyclic sugars and non-bicyclic sugars. As used herein, "sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or nucleic acids.

As used herein, "target nucleic acid," "target RNA," "target RNA transcript" and "nucleic acid target" mean a nucleic acid that a compound (e.g., an antisense compound) is designed to affect.

As used herein, "target region" means a portion of a target nucleic acid to which an antisense compound is designed to hybridize.

As used herein, "terminal group" means a chemical group or group of atoms that is covalently linked to a terminus of an oligonucleotide.

As used herein, "treat" refers to administering a compound or pharmaceutical composition to a human or non-human animal in order to effect an alteration or improvement of a disease, disorder, or condition in the animal.

I. Certain Oligonucleotides

In certain embodiments, the invention provides oligonucleotides, which consist of linked nucleosides. Oligonucleotides may be unmodified oligonucleotides (RNA or DNA) or may be modified oligonucleotides. Modified oligonucleotides comprise at least one modification relative to unmodified RNA or DNA (i.e., comprise at least one modified nucleoside (comprising a modified sugar moiety and/or a modified nucleobase) and/or at least one modified internucleoside linkage).

A. Certain Modified Nucleosides

Modified nucleosides comprise a modified sugar moiety or a modified nucleobase or both a modified sugar moiety and a modified nucleobase.

1. Certain Sugar Moieties

In certain embodiments, modified sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified sugar moieties comprising a furanosyl ring with one or more acyclic substituent, including but not limited to substituents at the 2', 4', and/or 5' positions. In certain embodiments one or more acyclic substituent of non-bicyclic modified sugar moieties is branched. Examples of 2'-substituent groups suitable for non-bicyclic modified sugar moieties include but are not limited to: 2'-F, 2'-OCH$_3$ ("OMe" or "O-methyl"), and 2'-O(CH$_2$)$_2$OCH$_3$ ("MOE"). In certain embodiments, 2'-substituent groups are selected from among: halo, allyl, amino, azido, SH, CN, OCN, CF$_3$, OCF$_3$, O—C$_1$-C$_{10}$ alkoxy, O—C$_1$-C$_{10}$ substituted alkoxy, O—C$_1$-C$_{10}$ alkyl, O—C$_1$-C$_{10}$ substituted alkyl, S-alkyl, N(R$_m$)-alkyl, O-alkenyl, S-alkenyl, N(R$_m$)-alkenyl, O-alkynyl, S-alkynyl, N(R$_m$)-alkynyl, O-alkylenyl-O-alkyl, alkynyl, alkaryl, aralkyl, O-alkaryl, O-aralkyl, O(CH$_2$)$_2$SCH$_3$, O(CH$_2$)$_2$ON(R$_m$)(R$_n$) or OCH$_2$C(=O)—N(R$_m$)(R$_n$), where each R$_m$ and R$_n$ is, independently, H, an amino protecting group, or substituted or unsubstituted C$_1$-C$_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro (NO$_2$), thiol, thioalkoxy, thioalkyl, halogen, alkyl, aryl, alkenyl and alkynyl. Examples of 4'-substituent groups suitable for non-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5'-methyl (R or S), 5'-vinyl, and 5'-methoxy. In certain embodiments, non-bicyclic modified sugars comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836.).

In certain embodiments, a 2'-substituted nucleoside or 2'-non-bicyclic modified nucleoside comprises a sugar moiety comprising a non-bridging 2'-substituent group selected from: F, NH$_2$, N$_3$, OCF$_3$, OCH$_3$, O(CH$_2$)$_3$NH$_2$, CH$_2$CH=CH$_2$, OCH$_2$CH=CH$_2$, OCH$_2$CH$_2$OCH$_3$, O(CH$_2$)$_2$SCH$_3$, O(CH$_2$)$_2$ON(R$_m$)(R$_n$), O(CH$_2$)$_2$O(CH$_2$)$_2$N(CH$_3$)$_2$, and N-substituted acetamide (OCH$_2$C(=O)—N(R$_m$)(R$_n$)), where each R$_m$ and R$_n$ is, independently, H, an amino protecting group, or substituted or unsubstituted C$_1$-C$_{10}$ alkyl.

In certain embodiments, a 2'-substituted nucleoside or 2'-non-bicyclic modified nucleoside comprises a sugar moiety comprising a non-bridging 2'-substituent group selected from: F, OCF$_3$, OCH$_3$, OCH$_2$CH$_2$OCH$_3$, O(CH$_2$)$_2$SCH$_3$, O(CH$_2$)$_2$ON(CH$_3$)$_2$, O(CH$_2$)$_2$O(CH$_2$)$_2$N(CH$_3$)$_2$, and OCH$_2$C(=O)—N(H)CH$_3$ ("NMA").

In certain embodiments, a 2'-substituted nucleoside or 2'-non-bicyclic modified nucleoside comprises a sugar moiety comprising a non-bridging 2'-substituent group selected from: F, OCH$_3$, and OCH$_2$CH$_2$OCH$_3$.

Nucleosides comprising modified sugar moieties, such as non-bicyclic modified sugar moieties, may be referred to by the position(s) of the substitution(s) on the sugar moiety of the nucleoside. For example, nucleosides comprising 2'-substituted or 2-modified sugar moieties are referred to as 2'-substituted nucleosides or 2-modified nucleosides.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' bridging sugar substituents include but are not limited to: 4'-CH$_2$-2', 4'-(CH$_2$)$_2$-2', 4'-(CH$_2$)$_3$-2', 4'-CH$_2$—O-2' ("LNA"), 4'-CH$_2$—S-2', 4'-(CH$_2$)$_2$—O-2' ("ENA"), 4'-CH(CH$_3$)—O-2' (referred to as "constrained ethyl" or "cEt" when in the S configuration), 4'-CH$_2$—O—CH$_2$-2', 4'-CH$_2$—N(R)-2', 4'-CH(CH$_2$OCH$_3$)—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-C(CH$_3$)(CH$_3$)—O-2' and analogs thereof (see, e.g., Seth et al., U.S. Pat. No. 8,278,283), 4'-CH$_2$—N(OCH$_3$)-2' and analogs thereof (see, e.g., Prakash et al., U.S. Pat. No. 8,278,425), 4'-CH$_2$—O—N(CH$_3$)-2' (see, e.g., Allerson et al., U.S. Pat. No. 7,696,345 and Allerson et al., U.S. Pat. No. 8,124,745), 4'-CH$_2$—C(H)(CH$_3$)-2' (see, e.g., Zhou, et al., J. Org. Chem., 2009, 74, 118-134), 4'-CH$_2$—C(=CH$_2$)-2' and analogs thereof (see e.g., Seth et al., U.S. Pat. No. 8,278,426), 4'-C(R$_a$R$_b$)—N(R)'O-2', 4'-C(R$_a$R$_b$)—O—N(R)-2', 4'-CH$_2$—O—N(R)-2', and 4'-CH$_2$—N(R)—O-2', wherein each R, R$_a$, and R$_b$ is, independently, H, a protecting group, or C$_1$-C$_{12}$ alkyl (see, e.g. Imanishi et al., U.S. Pat. No. 7,427,672).

In certain embodiments, such 4' to 2' bridges independently comprise from 1 to 4 linked groups independently selected from: —[C(R$_a$)(R$_b$)]$_n$—, —[C(R$_a$)(R$_b$)]$_n$—O—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:
x is 0, 1, or 2;
n is 1, 2, 3, or 4;
each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J2 is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Additional bicyclic sugar moieties are known in the art, see, for example: Freier et al., *Nucleic Acids Research*, 1997, 25(22), 4429-4443, Albaek et al., *J Org. Chem.*, 2006, 71, 7731-7740, Singh et al., *Chem. Commun.*, 1998, 4, 455-456; Koshkin et al., *Tetrahedron*, 1998, 54, 3607-3630; Kumar et al., *Bioorg. Med. Chem. Lett.*, 1998, 8, 2219-2222; Singh et al., *J Org. Chem.*, 1998, 63, 10035-10039; Srivastava et al., *J Am. Chem. Soc.*, 20017, 129, 8362-8379; Wengel et al., U.S. Pat. No. 7,053,207; Imanishi et al., U.S. Pat. No. 6,268,490; Imanishi et al. U.S. Pat. No. 6,770,748; Imanishi et al., U.S. Pat. No. RE44,779; Wengel et al., U.S. Pat. No. 6,794,499; Wengel et al., U.S. Pat. No. 6,670,461; Wengel et al., U.S. Pat. No. 7,034,133; Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191; Torsten et al., WO 2004/106356; Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

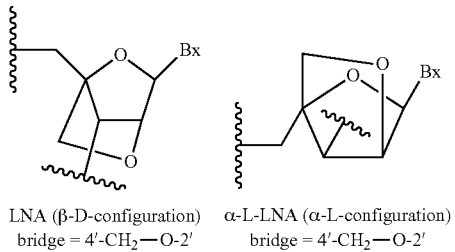

LNA (β-D-configuration)  α-L-LNA (α-L-configuration)
bridge = 4'-CH$_2$—O-2'  bridge = 4'-CH$_2$—O-2'

α-L-methyleneoxy (4'-CH$_2$—O-2') or α-L-LNA bicyclic nucleosides have been incorporated into antisense oligonucleotides that showed antisense activity (Frieden et al., *Nucleic Acids Research*, 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see, e.g., Leumann, C J. *Bioorg. & Med. Chem.* 2002, 10, 841-854), fluoro HNA:

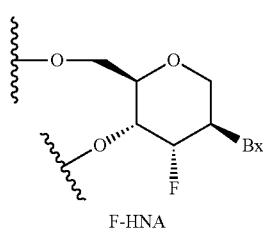

F-HNA ("F-HNA", see e.g. Swayze et al., U.S. Pat. No. 8,088,904; Swayze et al., U.S. Pat. No. 8,440,803; Swayze et al., U.S. Pat. No. 8,796,437; and Swayze et al., U.S. Pat. No. 9,005,906; F-HNA can also be referred to as a F-THP or 3'-fluoro tetrahydropyran), and nucleosides comprising additional modified THP compounds having the formula:

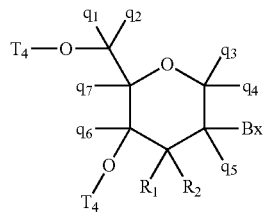

wherein, independently, for each of said modified THP nucleoside:

Bx is a nucleobase moiety;

T$_3$ and T4 are each, independently, an internucleoside linking group linking the modified THP nucleoside to the remainder of an oligonucleotide or one of T3 and T4 is an internucleoside linking group linking the modified THP nucleoside to the remainder of an oligonucleotide and the other of T3 and T4 is H, a hydroxyl protecting group, a linked conjugate group, or a 5' or 3'-terminal group; $q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

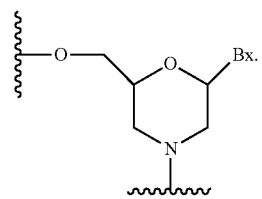

In certain embodiments, morpholinos may be modified, for example by adding or altering various substituent groups from the above morpholino structure. Such sugar surrogates are referred to herein as "modified morpholinos."

In certain embodiments, sugar surrogates comprise acyclic moieites. Examples of nucleosides and oligonucleotides comprising such acyclic sugar surrogates include but are not limited to: peptide nucleic acid ("PNA"), acyclic butyl nucleic acid (see, e.g., Kumar et al., *Org. Biomol. Chem.*, 2013, 11, 5853-5865), and nucleosides and oligonucleotides described in Manoharan et al., WO2011/133876.

Many other bicyclic and tricyclic sugar and sugar surrogate ring systems are known in the art that can be used in modified nucleosides.

2. Certain Modified Nucleobases

In certain embodiments, modified oligonucleotides comprise one or more nucleoside comprising an unmodified nucleobase. In certain embodiments, modified oligonucleotides comprise one or more nucleoside comprising a modified nucleobase.

In certain embodiments, modified nucleobases are selected from: 5-substituted pyrimidines, 6-azapyrimidines, alkyl or alkynyl substituted pyrimidines, alkyl substituted purines, and N-2, N-6 and O-6 substituted purines. In certain embodiments, modified nucleobases are selected from: 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (—C≡C—CH$_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in *The Concise Encyclopedia Of Polymer Science And Engineering*, Kroschwitz, J. I., Ed., John Wiley & Sons, 1990, 858-859; Englisch et al., *Angewandte Chemie*, International Edition, 1991, 30, 613; Sanghvi, Y. S., Chapter 15, *Antisense Research and Applications*, Crooke, S. T. and Lebleu, B., Eds., CRC Press, 1993, 273-288; and those disclosed in Chapters 6 and 15, *Antisense Drug Technology*, Crooke S. T., Ed., CRC Press, 2008, 163-166 and 442-443.

Publications that teach the preparation of certain of the above noted modified nucleobases as well as other modified nucleobases include without limitation, Manohara et al., US2003/0158403; Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., 6,166,199; and Matteucci et al., U.S. Pat. No. 6,005,096.

B. Certain Modified Internucleoside Linkages

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include but are not limited to phosphates, which contain a phosphodiester bond ("P=O") (also referred to as unmodified or naturally occurring linkages), phosphotriesters, methylphosphonates, phosphoramidates, and phosphorothioates ("P=S"), and phosphorodithioates ("HS—P=S"). Representative non-phosphorus containing internucleoside linking groups include but are not limited to methylenemethylimino (—CH$_2$—N(CH$_3$)—O—CH$_2$—), thiodiester, thionocarbamate (—O—C(=O)(NH)—S—); siloxane (—O—SiH$_2$—O—); and N,N'-dimethylhydrazine (—CH$_2$—N(CH$_3$)—N(CH$_3$)—). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Representative chiral internucleoside linkages include but are not limited to alkylphosphonates and phosphorothioates. Methods of preparation of phosphorous-containing and non-phosphorous-containing internucleoside linkages are well known to those skilled in the art.

Neutral internucleoside linkages include, without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), methoxypropyl, and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

C. Certain Motifs

In certain embodiments, modified oligonucleotides comprise one or more modified nucleoside comprising a modified sugar. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

1. Certain Sugar Motifs

In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, modified oligonucleotides comprise or consist of a region having a gapmer motif, which comprises two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-5 nucleosides. In certain embodiments, the wings of a gapmer comprise 2-5 nucleosides. In certain embodiments, the wings of a gapmer comprise 3-5 nucleosides. In certain embodiments, the nucleosides of a gapmer are all modified nucleosides.

In certain embodiments, the gap of a gapmer comprises 7-12 nucleosides. In certain embodiments, the gap of a gapmer comprises 7-10 nucleosides. In certain embodiments, the gap of a gapmer comprises 8-10 nucleosides. In certain embodiments, the gap of a gapmer comprises 10 nucleosides. In certain embodiment, each nucleoside of the gap of a gapmer is an unmodified 2'-deoxy nucleoside.

In certain embodiments, the gapmer is a deoxy gapmer. In such embodiments, the nucleosides on the gap side of each wing/gap junction are unmodified 2'-deoxynucleosides and the nucleosides on the wing sides of each wing/gap junction are modified nucleosides. In certain such embodiments, each nucleoside of the gap is an unmodified 2'-deoxynucleoside. In certain such embodiments, each nucleoside of each wing is a modified nucleoside.

In certain embodiments, modified oligonucleotides comprise or consist of a region having a fully modified sugar motif. In such embodiments, each nucleoside of the fully modified region of the modified oligonucleotide comprises a modified sugar moiety. In certain such embodiments, each nucleoside to the entire modified oligonucleotide comprises a modified sugar moiety. In certain embodiments, modified oligonucleotides comprise or consist of a region having a fully modified sugar motif, wherein each nucleoside within the fully modified region comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified comprises the same 2'-modification.

2. Certain Nucleobase Motifs

In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methylcytosines.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of said nucleoside is a 2'-deoxyribosyl moiety. In certain embodiments, the modified nucleobase is selected from: a 2-thiopyrimidine and a 5-propynepyrimidine.

3. Certain Internucleoside Linkage Motifs

In certain embodiments, oligonucleotides comprise modified and/or unmodified internucleoside linkages arranged along the oligonucleotide or region thereof in a defined pattern or motif. In certain embodiments, essentially each internucleoside linking group is a phosphate internucleoside linkage (P=O). In certain embodiments, each internucleoside linking group of a modified oligonucleotide is a phosphorothioate (P=S). In certain embodiments, each internucleoside linking group of a modified oligonucleotide is independently selected from a phosphorothioate and phosphate internucleoside linkage. In certain embodiments, the sugar motif of a modified oligonucleotide is a gapmer and the internucleoside linkages within the gap are all modified. In certain such embodiments, some or all of the internucleoside linkages in the wings are unmodified phosphate linkages. In certain embodiments, the terminal internucleoside linkages are modified.

D. Certain Lengths

In certain embodiments, oligonucleotides (including modified oligonucleotides) can have any of a variety of ranges of lengths. In certain embodiments, oligonucleotides consist of X to Y linked nucleosides, where X represents the fewest number of nucleosides in the range and Y represents the largest number nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, oligonucleotides consist of 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides E. Certain Modified Oligonucleotides In certain embodiments, the above modifications (sugar, nucleobase, internucleoside linkage) are incorporated into a modified oligonucleotide. In certain embodiments, modified oligonucleotides are characterized by their modification motifs and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such sugar gapmer oligonucleotides may comprise one or more modified nucleobase independent of the gapmer pattern of the sugar modifications. Furthermore, in certain instances, an oligonucleotide is described by an overall length or range and by lengths or length ranges of two or more regions (e.g., a regions of nucleosides having specified sugar modifications), in such circumstances it may be possible to select numbers for each range that result in an oligonucleotide having an overall length falling outside the specified range. In such circumstances, both elements must be satisfied. For example, in certain embodiments, a modified oligonucleotide consists if of 15-20 linked nucleosides and has a sugar motif consisting of three regions, A, B, and C, wherein region A consists of 2-6 linked nucleosides having a specified sugar motif, region B consists of 6-10 linked nucleosides having a specified sugar motif, and region C consists of 2-6 linked nucleosides having a specified sugar motif. Such embodiments do not include modified oligonucleotides where A and C each consist of 6 linked nucleosides and B consists of 10 linked nucleosides (even though those numbers of nucleosides are permitted within the requirements for A, B, and C) because the overall length of such oligonucleotide is 22, which exceeds the upper limit of the overall length of the modified oligonucleotide (20). Herein, if a description of an oligonucleotide is silent with respect to one or more parameter, such parameter is not limited. Thus, a modified oligonucleotide described only as having a gapmer sugar motif without further description may have any length, internucleoside linkage motif, and nucleobase motif. Unless otherwise indicated, all modifications are independent of nucleobase sequence.

F. Nucleobase Sequence

In certain embodiments, oligonucleotides (unmodified or modified oligonucleotides) are further described by their nucleobase sequence. In certain embodiments oligonucleotides have a nucleobase sequence that is complementary to a second oligonucleotide or an identified reference nucleic acid, such as a target nucleic acid. In certain such embodiments, a region of an oligonucleotide has a nucleobase sequence that is complementary to a second oligonucleotide or an identified reference nucleic acid, such as a target nucleic acid. In certain embodiments, the nucleobase sequence of a region or entire length of an oligonucleotide is at least 50%, at least 60%, at least 70%, at least 80%, at least 90%, at least 95%, or 100% complementary to the second oligonucleotide or nucleic acid, such as a target nucleic acid.

II. Certain Oligomeric Compounds

In certain embodiments, the invention provides oligomeric compounds, which consist of an oligonucleotide (modified or unmodified) and optionally one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphate moieties, protecting groups, abasic nucleosides, modified or unmodified nucleosides, and two or more nucleosides that are independently modified or unmodified.

A. Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance. In certain embodiments, conjugate groups impart a new property on the attached oligonucleotide, e.g., fluorophores or reporter groups that enable detection of the oligonucleotide. Certain conjugate groups and conjugate moieties have been described previously, for example: cholesterol moiety (Letsinger et al., Proc. Natl. Acad. Sci. USA, 1989, 86, 6553-6556), cholic acid (Manoharan et al., *Bioorg. Med. Chem. Lett.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med. Chem. Lett.,* 1993, 3, 2765-2770), a thiocholesterol (Oberhauser et al., *Nucl. Acids Res.,* 1992, 20, 533-538), an aliphatic chain, e.g., do-decan-diol or undecyl residues (Saison-Behmoaras et al., *EMBO J.*, 1, 1991, 10, 1111-1118; Kabanov et al., *FEBS Lett.*, 1990, 259, 327-330; Svinarchuk et al., *Biochimie*, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36, 3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic acid, a palmityl moiety (Mishra et al., *Biochim. Biophys. Acta*, 1995, 1264, 229-237), an octadecylamine or hexylamino-carbonyl-oxycholesterol moiety (Crooke et al., *J Pharmacol. Exp. Ther.*, 1996, 277, 923-937), a tocopherol group (Nishina et al., *Molecular Therapy Nucleic Acids*, 2015, 4, e220; and Nishina et al., *Molecular Therapy*, 2008, 16, 734-740), or a GalNAc cluster (e.g., WO2014/179620).

1. Conjugate Moieties

Conjugate moieties include, without limitation, intercalators, reporter molecules, polyamines, polyamides, peptides, carbohydrates (e.g., GalNAc), vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain oligomeric compounds, the conjugate linker is a single chemical bond (i.e., the conjugate moiety is attached directly to an oligonucleotide through a single bond). In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the oligonucleotides provided herein. In general, a bifunctional linking moiety comprises at least two functional groups. One of the functional groups is selected to bind to a particular site on a parent compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine. It is typically desirable for linker-nucleosides to be cleaved from the oligomeric compound after it reaches a target tissue. Accordingly, linker-nucleosides are typically linked to one another and to the remainder of the oligomeric compound through cleavable bonds. In certain embodimements, such cleavable bonds are phosphodiester bonds.

Herein, linker-nucleosides are not considered to be part of the oligonucleotide. Accordingly, in embodiments in which an oligomeric compound comprises an oligonucleotide consisting of a specified number or range of linked nucleosides and/or a specified percent complementarity to a reference nucleic acid and the oligomeric compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, an oligomeric compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such an oligomeric compound is more than 30. Alternatively, an oligomeric compound may comprise a modified oligonucleotide consisting of 8-30 nucleosides and no conjugate group. The total number of contiguous linked nucleosides in such an oligomeric compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances oligomeric compounds comprising a particular conjugate moiety are better taken up by a particular cell type, but once the oligomeric compound has been taken up, it is desirable that the conjugate group be cleaved to release the unconjugated or parent oligonucleotide. Thus, certain conjugate linkers may comprise one or more cleavable moieties. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate linkage between an oligonucleotide and a conjugate moiety or conjugate group.

In certain embodiments, a cleavable moiety comprises or consists of one or more linker-nucleosides. In certain such embodiments, the one or more linker-nucleosides are linked to one another and/or to the remainder of the oligomeric compound through cleavable bonds. In certain embodiments, such cleavable bonds are unmodified phosphodiester bonds. In certain embodiments, a cleavable moiety is 2'-deoxynucleoside that is attached to either the 3' or 5'-terminal nucleoside of an oligonucleotide by a phosphate internucleoside linkage and covalently attached to the remainder of the conjugate linker or conjugate moiety by a phosphate or phosphorothioate linkage. In certain such embodiments, the cleavable moiety is 2'-deoxyadenosine.

III. Certain Antisense Compounds

In certain embodiments, the present invention provides compounds, which comprise or consist of an oligomeric compound comprising an antisense oligonucleotide, having a nucleobase sequences complementary to that of a target nucleic acid. Certain such compounds are antisense compounds. In certain embodiments, antisense compounds are single-stranded. Such single-stranded antisense compounds typically comprise or consist of an oligomeric compound that comprises or consists of a modified oligonucleotide and optionally a conjugate group. In certain embodiments, antisense compounds are double-stranded. Such double-stranded antisense compounds comprise a first oligomeric compound having a region complementary to a target nucleic acid and a second oligomeric compound having a region complementary to the first oligomeric compound. The first oligomeric compound of such double stranded antisense compounds typically comprises or consists of a modified oligonucleotide and optionally a conjugate group. The oligonucleotide of the second oligomeric compound of such double-stranded antisense compound may be modified or unmodified. Either or both oligomeric compounds of a double-stranded antisense compound may comprise a conjugate group. The oligomeric compounds of double-stranded antisense compounds may include non-complementary overhanging nucleosides.

In certain embodiments, oligomeric compounds of antisense compounds are capable of hybridizing to a target nucleic acid, resulting in at least one antisense activity. In certain embodiments, antisense compounds selectively affect one or more target nucleic acid. Such selective antisense compounds comprises a nucleobase sequence that hybridizes to one or more target nucleic acid, resulting in one or more desired antisense activity and does not hybridize to one or more non-target nucleic acid or does not hybridize to one or more non-target nucleic acid in such a way that results in significant undesired antisense activity.

In certain antisense activities, hybridization of an antisense compound to a target nucleic acid results in recruitment of a protein that cleaves the target nucleic acid. For example, certain antisense compounds result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, the invention provides antisense compounds that are sufficiently "DNA-like" to elicit RNase H activity. Further, in certain embodiments, one or more non-DNA-like nucleoside in the gap of a gapmer is tolerated.

In certain antisense activities, an antisense compound or a portion of an antisense compound is loaded into an RNA-induced silencing complex (RISC), ultimately resulting in cleavage of the target nucleic acid. For example, certain antisense compounds result in cleavage of the target nucleic acid by Argonaute. Antisense compounds that are loaded into RISC are RNAi compounds. RNAi compounds may be double-stranded (siRNA) or single-stranded (ssRNA).

In certain embodiments, hybridization of an antisense compound to a target nucleic acid does not result in recruitment of a protein that cleaves that target nucleic acid. In certain such embodiments, hybridization of the antisense compound to the target nucleic acid results in alteration of splicing of the target nucleic acid. In certain embodiments, hybridization of an antisense compound to a target nucleic acid results in inhibition of a binding interaction between the target nucleic acid and a protein or other nucleic acid. In certain such embodiments, hybridization of an antisense compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein, and/or a phenotypic change in a cell or animal IV. Certain Target Nucleic Acids In certain embodiments, antisense compounds comprise or consist of an oligonucleotide comprising a region that is complementary to a target nucleic acid. In certain embodiments, the target nucleic acid is an endogenous RNA molecule. In certain embodiments, the target nucleic acid encodes a protein. In certain such embodiments, the target nucleic acid is selected from: an mRNA and a pre-mRNA, including intronic, exonic and untranslated regions. In certain embodiments, the target RNA is an mRNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron.

In certain embodiments, the target nucleic acid is a non-coding RNA. In certain such embodiments, the target non-coding RNA is selected from: a long-non-coding RNA, a short non-coding RNA, an intronic RNA molecule, a snoRNA, a scaRNA, a microRNA (including pre-microRNA and mature microRNA), a ribosomal RNA, and promoter directed RNA. In certain embodiments, the target nucleic acid is a nucleic acid other than a mature mRNA. In certain embodiments, the target nucleic acid is a nucleic acid other than a mature mRNA or a microRNA. In certain embodiments, the target nucleic acid is a non-coding RNA other than a microRNA. In certain embodiments, the target nucleic acid is a non-coding RNA other than a microRNA or an intronic region of a pre-mRNA. In certain embodiments, the target nucleic acid is a long non-coding RNA. In certain embodiments, the target nucleic acid is a non-coding RNA associated with splicing of other pre-mRNAs. In certain embodiments, the target nucleic acid is a nuclear-retained non-coding RNA.

In certain embodiments, antisense compounds described herein are complementary to a target nucleic acid comprising a single-nucleotide polymorphism (SNP). In certain such embodiments, the antisense compound is capable of modulating expression of one allele of the SNP-containing target nucleic acid to a greater or lesser extent than it modulates another allele. In certain embodiments, an antisense compound hybridizes to a (SNP)-containing target nucleic acid at the single-nucleotide polymorphism site.

In certain embodiments, antisense compounds are at least partially complementary to more than one target nucleic acid. For example, antisense compounds of the present invention may mimic microRNAs, which typically bind to multiple targets.

A. Complementarity/Mismatches to the Target Nucleic Acid

In certain embodiments, antisense compounds comprise antisense oligonucleotides that are complementary to the target nucleic acid over the entire length of the oligonucleotide. In certain embodiments, such oligonucleotides are 99% complementary to the target nucleic acid. In certain embodiments, such oligonucleotides are 95% complementary to the target nucleic acid. In certain embodiments, such oligonucleotides are 90% complementary to the target nucleic acid. In certain embodiments, such oligonucleotides are 85% complementary to the target nucleic acid. In certain embodiments, such oligonucleotides are 80% complementary to the target nucleic acid. In certain embodiments, antisense oligonucleotides are at least 80% complementary to the target nucleic acid over the entire length of the oligonucleotide and comprise a region that is 100% or fully complementary to a target nucleic acid. In certain such embodiments, the region of full complementarity is from 6 to 20 nucleobases in length. In certain such embodiments, the region of full complementarity is from 10 to 18 nucleobases in length. In certain such embodiments, the region of full complementarity is from 18 to 20 nucleobases in length.

In certain embodiments, the oligomeric compounds of antisense compounds comprise one or more mismatched nucleobases relative to the target nucleic acid. In certain such embodiments, antisense activity against the target is reduced by such mismatch, but activity against a non-target is reduced by a greater amount. Thus, in certain such embodiments selectivity of the antisense compound is improved. In certain embodiments, the mismatch is specifically positioned within an oligonucleotide having a gapmer motif. In certain such embodiments, the mismatch is at position 1, 2, 3, 4, 5, 6, 7, or 8 from the 5'-end of the gap region. In certain such embodiments, the mismatch is at position 9, 8, 7, 6, 5, 4, 3, 2, 1 from the 3'-end of the gap region. In certain such embodiments, the mismatch is at position 1, 2, 3, or 4 from the 5'-end of the wing region. In certain such embodiments, the mismatch is at position 4, 3, 2, or 1 from the 3'-end of the wing region.

B. PMP22

In certain embodiments, antisense compounds and oligomeric compounds comprise or consist of an oligonucleotide comprising a region that is complementary to a target nucleic acid, wherein the target nucleic acid is PMP22. In certain embodiments, a PMP22 nucleic acid has the sequence set forth in GENBANK Accession No. NM_000304.3 (incorporated herein as SEQ ID NO: 1).

In certain embodiments, contacting a cell with an antisense compound or oligomeric compound complementary to PMP22 reduces the amount of PMP22. In certain embodiments, contacting a cell with an antisense compound or oligomeric compound complementary to PMP22 reduces the amount of PMP22 and ameliorates one or more symptoms of Charcot-Marie-Tooth Disease.

C. Certain Target Nucleic Acids in Certain Tissues

In certain embodiments, antisense compounds or oligomeric compounds comprise or consist of an oligonucleotide comprising a region that is complementary to a target nucleic acid, wherein the target nucleic acid is expressed in nerve cells and/or Schwann cells.

V. Certain Pharmaceutical Compositions

In certain embodiments, the present invention provides pharmaceutical compositions comprising one or more antisense compound or a salt thereof. In certain such embodiments, the pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one antisense compound and sterile water. In certain embodiments, the sterile water is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile PBS. In certain embodiments, the sterile PBS is pharmaceutical grade PBS.

In certain embodiments, pharmaceutical compositions comprise one or more or antisense compound and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

In certain embodiments, pharmaceutical compositions comprising an antisense compound encompass any pharmaceutically acceptable salts of the antisense compound, esters of the antisense compound, or salts of such esters. In certain embodiments, pharmaceutical compositions comprising antisense compounds comprising one or more antisense oligonucleotide, upon administration to an animal, including a human, are capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts. In certain embodiments, prodrugs comprise one or more conjugate group attached to an oligonucleotide, wherein the conjugate group is cleaved by endogenous nucleases within the body.

Lipid moieties have been used in nucleic acid therapies in a variety of methods. In certain such methods, the nucleic acid, such as an antisense compound, is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions comprise a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, pharmaceutical compositions comprise one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, pharmaceutical compositions comprise a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, pharmaceutical compositions are prepared for oral administration. In certain embodiments, pharmaceutical compositions are prepared for buccal administration. In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain.

VI. Certain Routes of Administration

In certain embodiments, the compounds and compositions of the present disclosure are administered systemically. In certain such embodiments, the administration is subcutaneous. In certain embodiments, administration is parenteral. In certain embodiments, the route of administration leads to the administered compound reaching the peripheral nerves.

Nonlimiting Disclosure

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH in place of one 2'-H of DNA) or as an RNA having a modified base (thymine (methylated uracil) in place of a uracil of RNA). Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified nucleobases, such as "AT$^m$CGAUCG," wherein $^m$C indicates a cytosine base comprising a methyl group at the 5-position.

Certain compounds described herein (e.g., modified oligonucleotides) have one or more asymmetric center and thus give rise to enantiomers, diastereomers, and other stereoisomeric configurations that may be defined, in terms of absolute stereochemistry, as (R) or (S), or as (D) or (L), such as for amino acids, etc. Included in the compounds provided herein are all such possible isomers, including their racemic and optically pure forms, unless specified otherwise. Likewise, all cis- and trans-isomers and tautomeric forms are also included unless otherwise indicated.

The compounds described herein include variations in which one or more atoms are replaced with a non-radioactive isotope or radioactive isotope of the indicated element. For example, compounds herein that comprise hydrogen atoms encompass all possible deuterium substitutions for each of the $^1$H hydrogen atoms. Isotopic substitutions encompassed by the compounds herein include but are not limited to: $^2$H or $^3$H in place of $^1$H, $^{13}$C or $^{14}$C in place of $^{12}$C, $^{15}$N in place of $^{14}$N, $^{17}$O or $^{18}$O in place of $^{16}$O, and $^{33}$S, $^{34}$S, $^{35}$S, or $^{36}$S in place of $^{32}$S. In certain embodiments, non-radioactive isotopic substitutions may impart new properties on the oligomeric compound that are beneficial for use as a therapeutic or research tool. In certain embodiments, radioactive isotopic substitutions may make the compound suitable for research or diagnostic purposes such as imaging.

EXAMPLES

Example 1

Antisense Inhibition of Human PMP22 RNA In Vivo

The modified oligonucleotides listed in the tables below were tested for their effects on inhibition of PMP22 RNA in the sciatic nerves of C22 mice, which express human PMP22 and endogenous mouse PMP22 (see Example 2 below). The modified oligonucleotides listed in the table below are 3-10-3 cEt gapmers, wherein the central gap segment of each gapmer consists of ten 2'-deoxynucleosides and is flanked by wing segments on the 5' direction and the 3' direction consisting of three nucleosides each. Each nucleoside in the 5' wing segment and each nucleoside in the 3' wing segment has a cEt modification. All internucleoside linkages throughout each modified oligonucleotide are phosphorothioate linkages, and all cytosine residues are 5-methylcytosines. The modified oligonucleotides are complementary to human Peripheral Myelin Protein 22 (PMP22) mRNA sequence, designated herein as SEQ ID NO: 1 (GENBANK Accession No. NM_000304.3), and/or mouse PMP22 mRNA sequence, designated herein as SEQ ID NO: 2 (GENBANK Accession No. NM_001302255.1). The start and stop sites listed in the tables below refer to the 5' most position and 3' most position, respectively, to which each modified oligonucleotide is complementary on the indicated target PMP22 sequence. An asterisk indicates that the modified oligonucleotide has one mismatch relative to the indicated target sequence. An entry of "N/A" indicates that the modified oligonucleotide is not complementary to the indicated target sequence.

6-7 week old (Table 1) or 10 week old (Table 2) C22 mice each received weekly subcutaneous injections of 50 mg/kg of one of the modified oligonucleotides listed in the tables below or PBS vehicle alone. The injections were administered for 4 weeks, for a total of 5 injections per mouse. Each treatment group consisted of three or four mice except for one PBS control group, which consisted of two mice. Two to three days following the fifth injection, the mice were sacrificed, and the sciatic nerves were collected. Total RNA was isolated from the sciatic nerves and PMP22 mRNA levels were measured by RT-qPCR using human primer probe set LTS35382 (forward primer: CTCCTCCTGTTGCTGAGTATC, designated herein as SEQ ID NO: 3; reverse primer: GCTACAGTTCTGCCAGAGA, designated herein as SEQ ID NO: 4; probe: CAGTTGCGTGTCCATTGCCCA, designated herein as SEQ ID NO: 5) and mouse primer robe set LTS01148 (forward primer: CCGCAGCACAGCTGTCTTT, designated herein as SEQ ID NO: 6; reverse primer: AGCAGATTAGCCTCAGGCACAA, designated herein as SEQ ID NO: 7; probe: CCAGCAACCCAGTGGACGCACC, designated herein as SEQ ID NO: 8). PMP22 mRNA levels were normalized to Cyclophilin levels. Results are presented in the tables below as percent normalized PMP22 mRNA levels, relative to PBS treated mice. "N.D." indicates that the experiment was not performed.

TABLE 1

Antisense inhibition of PMP22 RNA in vivo

| Isis No. | Sequence | Hu PMP22 Start site | Hu PMP22 Stop site | Mouse PMP22 Start site | Mouse PMP22 Stop site | Hu PMP22 mRNA (%) | Mouse PMP22 mRNA (%) | SEQ ID NO. |
|---|---|---|---|---|---|---|---|---|
| 596929 | TGACGATGGTGGAGAC | 299* | 314 | 298 | 313 | 125 | 111 | 9 |
| 684394 | ATTATTCAGGTCTCCA | 1489 | 1504 | N/A | N/A | 47 | 92 | 10 |
| 684440 | ACAAGTCATTGCCAGA | 1705 | 1720 | 1697* | 1712 | 109 | 127 | 11 |
| 684446 | ATCTACAGTTGGTGGC | 1725 | 1740 | 1717 | 1732 | 114 | 127 | 12 |
| 718291 | CACTCATCACGCACAG | 560 | 575 | 559 | 574 | 121 | 115 | 13 |
| 718292 | GCACTCATCACGCACA | 561 | 576 | 560 | 575 | 87 | 113 | 14 |
| 718294 | CTTCAATCAACAGCAA | 862 | 877 | 877 | 892 | 126 | 125 | 15 |

TABLE 2

Antisense inhibition of PMP22 RNA in vivo

| Isis No. | Sequence | Hu PMP22 Start site | Hu PMP22 Stop site | Mouse PMP22 Start site | Mouse PMP22 Stop site | Hu PMP22 mRNA (%) | Mouse PMP22 mRNA (%) | SEQ ID NO. |
|---|---|---|---|---|---|---|---|---|
| 684267 | ATCTTCAATCAACAGC | 864 | 879 | 879 | 894 | 83 | N.D. | 16 |
| 684394 | ATTATTCAGGTCTCCA | 1489 | 1504 | N/A | N/A | 45 | N.D. | 10 |

Example 2

Effects of Antisense Inhibition of PMP22 RNA In Vivo

C22 mice, described in Huxley et al., *Human Molecular Genetics*, 5, 563-569 (1996) and Verhamme et al., *Journal of Neuropathology and Experimental Neurology*, 70, 386-398 (2011), express endogenous mouse PMP22 and overexpress a human PMP22 transgene. The C22 mice exhibit a phenotype that is more severe than the typical presentation of Charcot-Marie-Tooth Disease, Type 1A (CMT1A) in humans. Many pathological and electrophysiological features of CMT1A in humans are observed in the C22 mice, including demyelination, slowed motor nerve conduction velocity (MNCV), and reduced compound muscle action potential (CMAP). All of these features are evident by 3-4 weeks of age in C22 mice. The effects of antisense inhibition of human PMP22 RNA were tested in symptomatic C22 mice. First, the baseline (BL) grip strength, MNCV, and rotarod performance were assessed in 5-6 week old C22 and wild type (WT) mice. Following the baseline assessments, C22 mice were treated once per week with Isis No. 684267 in PBS at a dose listed in the tables below or PBS alone via subcutaneous injection. WT mice received no treatment. Each treatment group consisted of eight mice, four of which were male and four of which were female. At three, six, and nine weeks following the first dose of Isis No. 684267, grip strength and rotarod performance were assessed in all mice. MNCV of the sciatic nerve was assessed at three and nine weeks after first dose, and CMAP was measured at nine weeks after first dose. The mice were sacrificed after the last assessment, and human PMP22 mRNA levels in the sciatic nerve were measured by RT-qPCR. Myelination of the sciatic nerve was also assessed using histology.

Hindlimb Grip Strength

Mice were habituated in the behavioral room for 1 hour before the test. Mice were placed individually on the Grip-strength Meter (Columbus Instruments, Columbus, Ohio), and hindlimb grip strength was measured according to the manufacturer's instructions. The mice were pulled away from the wire, and the force applied to the wire just before each mouse lost its grip was recorded. The results for each treatment group are presented in the table below as the average force in grams applied just before the mice lost their grip.

Rotarod

After habituation in the test room, motor coordination was measured using an accelerating rotarod apparatus (Ugo Basile, Varese, Italy). Mice were first trained on a constant accelerating rod at 2 rpm for 2 minutes in 2 separate trials. All mice that passed these training trials were then put on the rotarod that accelerated from 4 to 40 rpm in 3 minutes. The time that it took for each mouse to fall from the accelerating rod (latency to fall) was recorded. The results are shown in the table below as the average latency to fall for each treatment group.

RT-qPCR

Total RNA was isolated from the sciatic nerves of the C22 mice. Isis No. 684267 is 100% complementary to both human and mouse PMP22 transcripts. Human PMP22 mRNA levels were measured by RT-qPCR using human primer probe set LTS35382 (see Example 1), and mouse PMP22 mRNA levels were measured by RT-qPCR using mouse primer probe set LTS01148 (see Example 1). PMP22 mRNA levels were normalized to Cyclophilin levels. Results are presented in the table below as average percent normalized PMP22 mRNA levels for each treatment group, relative to the PBS treated C22 treatment group.

Electrophysiology (MNCV and CMAP)

Electrophysiology was performed as described in Verhamme et al., *Journal of Neuropathology and Experimental Neurology*, 70, 386-398 (2011), with some modifications. Briefly, mice were anesthetized with 3% isoflurane, and maintained under anesthesia with 2% isoflurane in 100% oxygen. Body temperature was maintained above 35° C. by placing the mouse on a heating pad. VikingQuest EMG machine (Nicolet, Madison, Wis.) was used for MNCV and CMAP measurements. 27 G subdermal needle electrodes were used for stimulation and recording of responses. Stimulating cathodes were inserted through the skin at the sciatic notch (proximal site) and the medial ankle (distal site), which was 10 mm away from the sciatic notch; stimulating anode was inserted 3 mm distal to the stimulating cathode. The recording cathode was inserted through the skin past the tibialis anterior muscle, such that the needle just touched this muscle group, while the ground electrode was inserted through the skin halfway between the distal stimulating and recording electrodes. Stimulus intensity of 2 mA in 0.1 ms duration was delivered. MNCV was calculated by dividing the difference in the distance (10 mm) between the 2 recording sites by the latencies recorded following the distal and proximal stimulations. The results are presented in the table below as the average MNCV for each treatment group. CMAP was recorded as the maximal amplitude of the response as the stimulus intensity at the distal stimulation site was incrementally increased to 10 mA. The CMAP results are presented in the table below as the average maximum amplitude recorded for each treatment group.

Myelination Status

Cross sections of the sciatic nerve were stained with Toluidine blue and the unmyelinated axons, myelinated axons, and onion bulbs were counted. The average results for each treatment group are presented in the table below as the percent of total axons counted that were unmyelinated, myelinated, or had an onion bulb.

TABLE 3

Motor function

| Mouse | Treatment | Dose | Grip strength (g) | | | | Rotarod (s) | | | |
|---|---|---|---|---|---|---|---|---|---|---|
| | | | BL | 3 wks | 6 wks | 9 wks | BL | 3 wks | 6 wks | 9 wks |
| WT | N/A | N/A | 103 | 122 | 113 | 129 | 162 | 176 | 180 | 179 |
| C22 | PBS | N/A | 60 | 51 | 38 | 42 | 85 | 92 | 71 | 69 |
| C22 | Isis No. 684267 | 25 mg/kg | 61 | 55 | 41 | 50 | 86 | 103 | 90 | 97 |
| C22 | Isis No. 684267 | 50 mg/kg | 59 | 55 | 48 | 62 | 81 | 97 | 91 | 94 |
| C22 | Isis No. 684267 | 100 mg/kg | 57 | 54 | 48 | 79 | 66 | 130 | 128 | 92 |

TABLE 4

PMP22 mRNA levels

| Mouse | Treatment | Dose | Human PMP22 mRNA (%) | Mouse PMP22 mRNA (%) |
|---|---|---|---|---|
| WT | N/A | N/A | N/A | 122 |
| C22 | PBS | N/A | 100 | 100 |
| C22 | Isis No. 684267 | 25 mg/kg | 86 | 78 |
| C22 | Isis No. 684267 | 50 mg/kg | 72 | 70 |
| C22 | Isis No. 684267 | 100 mg/kg | 55 | 65 |

TABLE 5

Nerve function

| Mouse | Treatment | Dose | MNCV (m/s) | | | CMAP (mV) |
|---|---|---|---|---|---|---|
| | | | BL | 3 wks | 9 wks | 9 wks |
| WT | N/A | N/A | 47 | 44 | 49 | 49.4 |
| C22 | PBS | N/A | 23 | 17 | 9 | 1.1 |
| C22 | Isis No. 684267 | 25 mg/kg | 22 | 21 | 42 | 2.6 |
| C22 | Isis No. 684267 | 50 mg/kg | 21 | 24 | 41 | 6.8 |
| C22 | Isis No. 684267 | 100 mg/kg | 17 | 21 | 35 | 12.3 |

TABLE 6

Myelination status

| Mouse | Treatment | Dose | Myelinated (%) | Unmyelinated (%) | Onion bulbs (%) |
|---|---|---|---|---|---|
| WT | N/A | N/A | 93.6 | 5.5 | 0.9 |
| C22 | PBS | N/A | 50.3 | 35.2 | 14.5 |
| C22 | Isis No. 684267 | 100 mg/kg | 77.5 | 20.5 | 2.0 |

The invention claimed is:

1. A method comprising administering an oligomeric compound comprising a modified oligonucleotide to an individual for treating, preventing, or ameliorating a disease associated with PMP22, wherein the modified oligonucleotide comprises a complementary region of at least 12 contiguous nucleobases, wherein the nucleobase sequence of the complementary region is complementary to a target region of a PMP22 transcript, and wherein the disease is Charcot-Marie-Tooth Disease.

2. The method of claim 1, wherein the nucleobase sequence of the modified oligonucleotide is at least 80% complementary to the target region of a PMP22 transcript.

3. The method of claim 1, wherein the modified oligonucleotide comprises at least one modified nucleoside.

4. The method of claim 3, wherein at least one modified nucleoside comprises a modified sugar moiety.

5. The method of claim 4, wherein at least one modified sugar moiety is a non-bicyclic, 2'-substituted sugar moiety.

6. The method of claim 5, wherein the non-bicyclic, 2'-substituted sugar moiety is selected from among 2'-OMe, 2'-F, and 2'-MOE.

7. The method of claim 4, wherein at least one modified sugar moiety is a bicyclic sugar moiety.

8. The method of claim 7, wherein at least one the bicyclic sugar moiety is selected from LNA or cEt.

9. The method of claim 4, wherein at least one modified sugar moiety is a sugar surrogate.

10. The method of claim 1, wherein the modified oligonucleotide comprises 16 linked nucleosides.

11. The method of claim 1, wherein the modified oligonucleotide consists of 16 linked nucleosides.

12. The method of claim 1, wherein the oligomeric compound comprises a conjugate group.

13. The method of claim 1, wherein the modified oligonucleotide comprises at least one modified internucleoside linkage.

14. The method of claim 13, wherein at least one modified internucleoside linkage is a phosphorothioate internucleoside linkage.

15. The method of claim 14, wherein each internucleoside linkage is a phosphorothioate internucleoside linkage.

16. The method of claim 1, wherein the oligomeric compound is single-stranded.

17. The method of claim 1, wherein the oligomeric compound is paired with a second oligomeric compound to form a duplex.

18. The method of claim 1, wherein the oligomeric compound is a pharmaceutically acceptable salt.

19. The method of claim 1, wherein the oligomeric compound is administered in a pharmaceutically acceptable carrier or diluent.

20. The method of claim 1, wherein the oligomeric compound is administered systemically.

21. The method of claim 1, wherein the oligomeric compound is administered subcutaneously.

22. The method of claim 1, wherein at least one symptom of the disease is alleviated.

23. The method of claim 1, wherein the rate of progression of at least one symptom of the disease is decreased.

24. The method of claim 1, wherein the disease is Charcot-Marie-Tooth Disease Type 1.

25. The method of claim 1, wherein the disease is Charcot-Marie-Tooth Disease Type 1A.

* * * * *

SEQUENCE LISTING

<160> NUMBER OF SEQ ID NOS: 16

<210> SEQ ID NO 1
<211> LENGTH: 1861
<212> TYPE: DNA
<213> ORGANISM: Homo sapiens

<400> SEQUENCE: 1

```
ataaaactgg aaagacgcct ggtctggctt cagttacagg gagcaccacc agggaacatc    60
tcggggagcc tggttggaag ctgcaggctt agtctgtcgg ctgcgggtct ctgactgccc   120
tgtggggagg tcttgccttt aacatccctt gcatttggct gcaaagaaat ctgcttggaa   180
gaaggggtta cgctgtttgg ccgggcagaa actccgctga gcagaacttg ccgccagaat   240
gctcctcctg ttgctgagta tcatcgtcct ccacgtcgcg gtgctggtgc tgctgttcgt   300
ctccacgatc gtcagccaat ggatcgtggg caatggacac gcaactgatc tctggcagaa   360
ctgtagcacc tcttcctcag gaaatgtcca ccactgtttc tcatcatcac caaacgaatg   420
gctgcagtct gtccaggcca ccatgatcct gtcgatcatc ttcagcattc tgtctctgtt   480
cctgttcttc tgccaactct tcaccctcac caagggggc aggttttaca tcactggaat   540
cttccaaatt cttgctggtc tgtgcgtgat gagtgctgcg gccatctaca ggtgaggca   600
cccggagtgg catctcaact cggattactc ctacggtttc gcctacatcc tggcctgggt   660
```

-continued

```
ggccttcccc ctggcccttc tcagcggtgt catctatgtg atcttgcgga aacgcgaatg      720
aggcgcccag acggtctgtc tgaggctctg agcgtacata gggaagggag gaagggaaaa      780
cagaaagcag acaaagaaaa aagagctagc ccaaaatccc aaactcaaac caaaccaaac      840
agaaagcagt ggaggtgggg gttgctgttg attgaagatg tatataatat ctccggttta      900
taaaacctat ttataacact ttttacatat atgtacatag tattgtttgc tttttatgtt      960
gaccatcagc ctcgtgttga gccttaaaga agtagctaag aactttaca tcctaacagt     1020 ataatccagc tcagtatttt tgttttgttt tttgtttgtt tgttttgttt tacccagaaa     1080
taagataact ccatctcgcc ccttcccttt catctgaaag aagatacctc cctcccagtc     1140
cacctcattt agaaaaccaa agtgtgggta gaaaccccaa atgtccaaaa gccctttct      1200 ggtgggtgac ccagtgcatc aacagaaac agccgctgcc cgaacctctg tgtgaagctt     1260
tacgcgcaca cggacaaaat gcccaaactg gagcccttgc aaaaacacgg cttgtggcat     1320
tggcatactt gcccttacag gtggagtatc ttcgtcacac atctaaatga gaaatcagtg     1380
acaacaagtc tttgaaatgg tgctatggat ttaccattcc ttattatcac taatcatcta     1440
aacaactcac tggaaatcca attaacaatt ttacaacata agatagaatg gagacctgaa     1500
taattctgtg taatataaat ggtttataac tgcttttgta cctagctagg ctgctattat     1560
tactataatg agtaaatcat aaagccttca tcactccac atttttctta cggtcggagc      1620
atcagaacaa gcgtctagac tccttgggac cgtgagttcc tagagcttgg ctgggtctag     1680
gctgttctgt gcctccaagg actgtctggc aatgacttgt attggccacc aactgtagat     1740
gtatatatgg tgcccttctg atgctaagac tccagacctt ttgttttgc tttgcattt      1800 ctgattttat accaactgtg tggactaaga tgcattaaaa taaacatcag agtaactcac     1860
t                                                                    1861
```

<210> SEQ ID NO 2
<211> LENGTH: 1862
<212> TYPE: DNA
<213> ORGANISM: Mus musculus

<400> SEQUENCE: 2

```
acacccttct gcagcgacgc aaatagggcg tagttcccgt taaaggggaa caccgggagc       60
ctcccactgc cccttgctt tgcgcgcgcg ctgacccgca gcacagctgt ctttggggac      120
gccagcaacc cagtggacgc accggagttt gtgcctgagg ctaatctgct ctgagatagc     180
tgtccctttg aactgaaagc accgctcctc tgatcccgag cccaactccc agccaccatg     240
ctcctactct tgttggggat cctgttcctg cacatcgcgg tgctagtgtt gctcttcgtc     300
tccaccatcg tcagccaatg gctcgtgggc aatggacaca cgactgatct ctggcagaac     360
tgtaccacat ccgccttggg agccgtccaa cactgctact cctcatcagt gagcgaatgg     420
ctgcagtctg tccaggccac catgatcctg tctgtcatct tcagcgtcct ggctctgttc     480
ctgttcttct gccagctctt cactctcacc aaaggcggcc ggttttacat cactggattc     540
ttccaaatcc ttgctggtct gtgcgtgatg agtgcagcgg ccatctacac agtgaggcac     600
agtgagtggc atgtcaacac tgactactcc tatggcttcg cctacatcct ggcctgggtg     660
gcctttcccc tagccctcct cagtggtatc atctatgtga tcctgcggaa acgcgaatga     720
ggcgcccgac gacgcaccgt ccgtctaggc tctgagcgcg catagggtcc acagggaggg     780
aggaaggaaa ccagagaaca aaaccaacca accaaaaag agctagcccc aaacccaaac     840
```

-continued

| | |
|---|---|
| gcaagccaaa ccaaacagaa cgcagttgag tggggattgc tgttgattga agatgtatat | 900 |
| aatatctatg gtttataaaa cctatttata acactttta catatatgta cataggattg | 960 |
| ttttgctttt tatgttgacc gtcagcctcg tgttgaatct taaacaactt tacatcctaa | 1020 |
| cactataacc aagctcagta tctttgtttt gtttcgtttt tttttttaat ctttttgttt | 1080 |
| tgctcagaca taaaaactcc acgtggcccc ctttcatctg aaagcagata cctccctccc | 1140 |
| actcaacctc ataggataac caaagtgtgg ggacaaaccc cagacagttg aagaccttta | 1200 |
| cactatgggt gacccagtgc atttagcagg agtatccact gcccgaatcc atgtgtgaag | 1260 |
| ccctaagcac tcacagacga aaagccctga ccggaaccct ctgcaaaaac agtaatagct | 1320 |
| ggtggctcct gaacacttga ccctgtagac ggagtactgg ggccacacgt ttaaatgaga | 1380 |
| agtcagagac aagcaatctg tgaaatggtg ctatagattt accattcctt gttattacta | 1440 |
| atcgtttaaa ccactcactg gaaactcaat taacagtttt atgcgataca gcagaatgga | 1500 |
| gacccgatac aaacggttca taactgcttt catacctagc taggctgttg ttattactac | 1560 |
| aataaataaa tctcaaagcc ttcgtcagtc ccacagtttt ctcacggtcg gagcatcagg | 1620 |
| acgagcatct agaccctgg gactagcgag ttccctggct ttctgggtct agagtgttct | 1680 |
| gtgcctccaa ggactgtctg gcgatgactt gtattggcca ccaactgtag atgtatatac | 1740 |
| ggtgtccttc tgatgctaag actccagacc tttcttgttt ttgcttgctt tctctgattt | 1800 |
| tataccaact gtgtggacta agatgcatca aaataaacat cagagtaact caaaaaaaaa | 1860 |
| aa | 1862 |

<210> SEQ ID NO 3
<211> LENGTH: 21
<212> TYPE: DNA
<213> ORGANISM: Artificial sequence
<220> FEATURE:
<223> OTHER INFORMATION: Primer

<400> SEQUENCE: 3

| | |
|---|---|
| ctcctcctgt tgctgagtat c | 21 |

<210> SEQ ID NO 4
<211> LENGTH: 19
<212> TYPE: DNA
<213> ORGANISM: Artificial sequence
<220> FEATURE:
<223> OTHER INFORMATION: Primer

<400> SEQUENCE: 4

| | |
|---|---|
| gctacagttc tgccagaga | 19 |

<210> SEQ ID NO 5
<211> LENGTH: 21
<212> TYPE: DNA
<213> ORGANISM: Artificial sequence
<220> FEATURE:
<223> OTHER INFORMATION: Probe

<400> SEQUENCE: 5

| | |
|---|---|
| cagttgcgtg tccattgccc a | 21 |

<210> SEQ ID NO 6
<211> LENGTH: 19
<212> TYPE: DNA
<213> ORGANISM: Artificial sequence
<220> FEATURE:
<223> OTHER INFORMATION: Primer

```
<400> SEQUENCE: 6
ccgcagcaca gctgtcttt                                              19

<210> SEQ ID NO 7
<211> LENGTH: 22
<212> TYPE: DNA
<213> ORGANISM: Artificial sequence
<220> FEATURE:
<223> OTHER INFORMATION: Primer

<400> SEQUENCE: 7
agcagattag cctcaggcac aa                                          22

<210> SEQ ID NO 8
<211> LENGTH: 22
<212> TYPE: DNA
<213> ORGANISM: Artificial sequence
<220> FEATURE:
<223> OTHER INFORMATION: Probe

<400> SEQUENCE: 8
ccagcaaccc agtggacgca cc                                          22

<210> SEQ ID NO 9
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 9
tgacgatggt ggagac                                                 16

<210> SEQ ID NO 10
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 10
attattcagg tctcca                                                 16

<210> SEQ ID NO 11
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 11
acaagtcatt gccaga                                                 16

<210> SEQ ID NO 12
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 12
atctacagtt ggtggc                                                 16

<210> SEQ ID NO 13
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 13
cactcatcac gcacag                                                    16

<210> SEQ ID NO 14
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 14
gcactcatca cgcaca                                                    16

<210> SEQ ID NO 15
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 15
cttcaatcaa cagcaa                                                    16

<210> SEQ ID NO 16
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 16
atcttcaatc aacagc                                                    16
```